(12) United States Patent
McGimpsey et al.

(10) Patent No.: US 7,326,526 B2
(45) Date of Patent: Feb. 5, 2008

(54) FILMS WITH PHOTORESPONSIVE WETTABILITY

(75) Inventors: W. Grant McGimpsey, Boylston, MA (US); John C. MacDonald, Jefferson, MA (US)

(73) Assignee: Worcester Polytechnic Institute, Worcester, MA (US)

(*) Notice: Subject to any disclaimer, the term of this patent is extended or adjusted under 35 U.S.C. 154(b) by 276 days.

(21) Appl. No.: 11/014,220

(22) Filed: Dec. 15, 2004

(65) Prior Publication Data

US 2005/0271975 A1 Dec. 8, 2005

Related U.S. Application Data

(60) Provisional application No. 60/530,023, filed on Dec. 15, 2003.

(51) Int. Cl.
| G03C 1/685 | (2006.01) |
| G03C 1/735 | (2006.01) |
| G03C 1/74 | (2006.01) |
| G03C 1/67 | (2006.01) |

(52) U.S. Cl. .............. 430/345; 430/327; 430/338; 430/962; 428/338

(58) Field of Classification Search .............. 430/338, 430/345, 962, 327; 428/338
See application file for complete search history.

(56) References Cited

U.S. PATENT DOCUMENTS

| 4,686,169 A * | 8/1987 | Yoshino et al. ............. 430/339 |
| 5,288,592 A * | 2/1994 | Miyashita ................... 430/345 |
| 6,433,270 B1 | 8/2002 | Rack |
| 6,740,409 B1 | 5/2004 | Granick et al. |
| 6,893,716 B2 * | 5/2005 | McGimpsey et al. ....... 428/333 |

| 2003/0071247 A1 | 4/2003 | Petrovskaia et al. |
| 2003/0104229 A1 | 6/2003 | Li et al. |
| 2003/0156244 A1 | 8/2003 | Canary et al. |
| 2004/0110009 A1 | 6/2004 | McGimpsey et al. |
| 2004/0131872 A1 | 7/2004 | Fan et al. |
| 2004/0185255 A1 | 9/2004 | Walters et al. |
| 2004/0191520 A1 | 9/2004 | Kumar et al. |

FOREIGN PATENT DOCUMENTS

| JP | 2001/051369 | 2/2001 |

(Continued)

OTHER PUBLICATIONS

Abbott, Scott, et al., "Reversible Wettability of Photoresponsive Pyrimidine-Coated Surfaces," *Langmuir*, vol. 15:8923-8928 (1999).

(Continued)

*Primary Examiner*—Richard L. Schilling
(74) *Attorney, Agent, or Firm*—Lahive & Cockfield LLP

(57) ABSTRACT

In various aspects, the present invention provides substantially monolayer thick molecular films with photoresponsive wettability, the molecules of said films comprising a photochromic molecule coordinated to a metal atom, which is coordinated to an organic tethering molecule, surface coupling group, or both, having a group for attachment to a surface of a substrate. In various aspects, the present inventions also provide photochromic articles comprising said films, methods of forming said films, and methods of manufacturing photochromic articles using said films. In various embodiments, provided are molecular films where the photoconversion between configurations of the photochromic molecule is substantially reversible by irradiation with light. In various embodiments, provided are films where the photoconversion is substantially irreversible by irradiation with light.

20 Claims, 23 Drawing Sheets

FOREIGN PATENT DOCUMENTS

| WO | WO-01/21727 A1 | 3/2001 |
|---|---|---|
| WO | WO-03/097765 A1 | 11/2003 |

OTHER PUBLICATIONS

Bouas-Laurent, Henri, et al., "Organic Photochromism," *Pure Appl. Chem.*, vol. 73(4):639-665 (2001).

Chen, L., et al., "Hole Transfer Equilibrium in Rigidly Linked Bichromophoric Molecules," *J. Phys. Chem. A.*, vol. 103:9167-9173 (1999).

Cooper, Christopher G.F., et al., "Non-Covalent Assembly of a Photoswitchable Surface," *J. Am. Chem. Soc.*, vol. 126:1032-1033 (2004).

Görner, Helmut, et al., "Complexes of spiropyran-derived merocyanines with metal ions Thermally activated and light-induced processes," *J. Chem. Soc.*, vol. 94(17):2557-2564 (1998).

Ishihara, Kazuhiko, et al., "Photo-Induced Change in Wettability and Binding Ability of Azoaromatic Polymers," *Journal of Applied Polymer Science*, vol. 27:239-245 (1982).

Ichimura, Kunihiro, et al., "Light-Driven Motion of Liquids on a Photoresponsive Surface," *Science*, vol. 288:1624-1626 (2000).

Kim, Sung-Hoon, et al., "The preparation and spectroscopic study of self-assembled monolayers of a UV-sensitive spiroxazine dye on gold," *Dyes and Pigments*, vol. 45:51-57 (2000).

McGimpsey, W.G., et al., "Singlet-Singlet, Triplet-Triplet, and 'Optically-Controlled' Energy Transfer in Polychromophores. Preliminary Models for a Molecular Scale Shift Register," *J. Phys. Chem.*, vol. 102:8679-8689 (1998).

McGimpsey, W.G., et al., "Singlet-Singlet and Tripet—Triplet Energy Transfer in Bichromophoric Peptides," *J. Phys. Chem. A.*, vol. 103:6082-6090 (1999).

Möller, G., et al., "Controlling Microdroplet Formation by Light," *The ACS Journal of Surfaces and Colloids*, vol. 14(18):4955-4957 (1998).

Rosario, Rohit, et al., "Photon-Modulated Wettability Changes on Spiropyran-Coated Surfaces," *Langmuir*, vol. 18:8062-8069 (2002).

Siewierski, L.M., et al., "Photoresponsive Monolayers Containing In-Chain Azobenzene," *Langmuir*, vol. 12:5838-5844 (1996).

Soto, Ernest, et al., "A Non-Covalent Strategy for the Assembly of Supramolecular Photocurrent-Generating Systems," *J. Am. Chem. Soc.*, vol. 125:2838-2839 (2003).

Tan, Z., et al., "Intramolecular Singlet—Singlet and Triplet—Triplet Energy Transfer in Adamantyl-Linked Trichromophores," *J. Phys. Chem. A.*, vol. 103:7612-7620 (1999).

Vansant, J., et al., "Azastilbenes. 2. Photodimerization," *J. Org. Chem.*, vol. 45:1565-1573 (1980).

International Search Report to PCT/US2004/042259 (Jun. 5, 2005), 15 pages.

Written Opinion of the International Search Authority for Application No. PCT/US2004/042259, dated Jun. 20, 2006.

* cited by examiner

*trans (anti)*        *cis (syn)*

Closed Form        Open Form

FILMS WITH PHOTORESPONSIVE WETTABILITY

CROSS-REFERENCE TO RELATED APPLICATIONS

The present application claims the benefit of U.S. Provisional Patent Application Ser. No. 60/530,023, filed Dec. 15, 2003, the entire contents of which are incorporated herein by reference.

BACKGROUND

The field of microfluidics has a number of emerging applications in analytical chemistry and chemical processing. One task central to the operation of microfluidic devices is the ability to move small volumes of fluid through microchannels and to control fluid flow. Traditional approaches to microfluidic device fabrication employ microfabrication or micromachining of substrates to produce three-dimensional structures to channel fluid flow. However, fabrication of such structures as valves, mixers and even chambers becomes increasingly difficult as the scale of the device decreases.

In addition, fluid transport and handling at sub-millimeter scales is distinctly different from such transport at larger scales. The large surface forces, high shear and extensional rates (e.g., low Reynolds number and high Weissenberg number), arising between the fluid and the microfluidic channels can make approaches and structures useful at larger scales useless or even inoperable at microfluidic scales. For example, as the size of the fluid conduits decrease it becomes increasingly harder to pump fluid by pressure. Surface-tension-driven actuation is one approach for handling liquids on sub-millimeter and smaller scale, but control of surface wettability can be problematic at these scales.

In addition, with decreasing scale, pumps and valves with moving parts become less attractive from an economic perspective. To this extent, functionalization of surfaces with covalently bound molecules has been attempted. However, such approaches may simply shift the primary determinant of device cost from the micromachining step to the synthesis of the covalently bound molecules and their proper attachment to the surface.

SUMMARY OF THE INVENTION

In various aspects, the present invention provides substantially monolayer thick films with photoresponsive wettability. In various embodiments, the films of the present invention can be used, for example, in the micro- and nano-manipulation of fluid motion and the fabrication of micro- and nanofluidic devices. For example, in various embodiments, the ability to alter the wettability of a film surface through irradiation with light can provide micro- and nanofluidic mixers, valves, pumps, channels, and chambers.

In various aspects, the present invention provides a substantially monolayer thick molecular film comprising a photochromic molecule bound via a metal atom to a self assembling molecule, the self assembling molecule having a surface coupling group for coupling the self assembling molecule to a surface of a substrate. In various embodiments, the photochromic molecule comprises one or more donor atoms coordinated to the metal atom and the self assembly molecule comprises a metal coupling group having one or more donor atoms coordinated to the metal atom; wherein, each donor atom is preferably independently oxygen (O) or nitrogen (N), and the metal atom is a transition metal atom, a lanthanide metal atom, or a lead atom (Pb).

In various embodiments, the surface coupling group and metal coupling group together comprise one or more of alkyloxy, alkylcarbonyl, amide, carboxyl, hydroxyl and pyridyl, when the surface of a substrate on which the substantially monolayer thick molecular film is attached comprises a polymer or plastic. In various embodiments, the surface coupling group and metal coupling group together comprise oxygen, when the surface of a substrate on which the substantially monolayer thick molecular film is attached comprises an ORMOSIL gel.

In various aspects, the present invention provides, a substantially monolayer thick molecular film comprising molecules of general formula (1) below,

$$R_1\text{-}M\text{-}R_2(X)_m R_3 R_4 \qquad (I),$$

the molecules being attached to a surface of a substrate substantially via $R_4$, wherein, $R_1$ represents a photochromic molecule coordinated to M;

M represents a transition metal atom substantially of oxidation state Y a lanthanide metal atom substantially of oxidation state Z or a lead (Pb) atom of oxidation state IV;

Y represents oxidation state I, II, III, IV, V, or VI;

Z represents oxidation state I, II, III, IV, V, or VI;

$R_2$ represents an unsubstituted heterocyclic group coordinated to M, a substituted heterocyclic group coordinated to M, or a substituted aryl group coordinated to M (wherein the substituted aryl group is substituted with one or of more oxygen, nitrogen or oxygen and nitrogen containing substituents from the substituent group A);

the dashed line represents the coordination of one or more donor atoms to M;

X represents a —NH—, —O—, or —S—;

m represents 0 or 1;

$R_3$ represents an alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof;

$R_4$ represents a bond, —O—, —S—, —P—, —CH$_2$—, —OSi(OR$_5$)$_2$ or —OSiCl$_2$—;

$R_5$ represents an alkyl; and substituent group A comprises an alkoxyl group, an amide group, an amino group, a carbonyl group, a carboxyl group, a hydroxyl group, and a heterocyclic group.

In various aspects, the present invention provides, a substantially monolayer thick molecular film comprising molecules of general formula (II) below,

$$R_1\text{-}M\text{-}R_2 \qquad (II),$$

the molecules being attached to a surface of a substrate substantially via $R_2$, wherein, the substrate surface comprises one or more of a polymer, plastic, or ORMOSIL gel;

$R_1$ represents a photochromic molecule coordinated to M;

M represents a transition metal atom substantially of oxidation state Y, a lanthanide metal atom substantially of oxidation state Z, or a lead (Pb) atom of oxidation state IV;

Y represents oxidation state I, II, III, IV, V, or VI;

Z represents oxidation state I, II, III, IV, V, or VI;

$R_2$ represents an oxygen atom, alkyloxy, alkylcarbonyl, amide, carboxyl, hydroxyl or pyridyl group with one or more oxygen, nitrogen or oxygen and nitrogen atoms coordinated to M; and the dashed line represents the coordination of one or more donor atoms to M.

In various aspects, the present invention provides photochromic articles comprising a substrate having a surface with a substantially monolayer thick molecular film covering at least a portion of the surface, the substantially monolayer thick molecular film having a photoresponsive wettability. The molecular film comprising molecules of the general formula (III): $R_1$-M-$R_2$(M)$_m$$R_3$$R_4$, the molecules being attached to a surface of a substrate via $R_4$, wherein, $R_1$ represents a photochromic molecule coordinated to M;

M represents a transition metal atom substantially of oxidation state Y a lanthanide metal atom substantially of oxidation state Z or a lead (Pb) atom of oxidation state IV;

Y represents oxidation state I, II, II, IV, V, or VI;

Z represents oxidation state I, II, II, IV, V, or VI;

$R_2$ represents an unsubstituted heterocyclic group coordinated to M, a substituted heterocyclic group coordinated to M, or a substituted aryl group coordinated to M (wherein the substituted aryl group is substituted with one or of more oxygen, nitrogen or oxygen and nitrogen containing substituents from the substituent group A);

the dashed line represents the coordination of one or more donor atoms to M;

X represents a —NH—, —O—, or —S—;

m represents 0 or 1;

$R_3$ represents an alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof;

$R_4$ represents a bond, —O—, —S—, —P—, —CH$_2$—, —OSi(OR$_5$)$_2$ or —OSiCl$_2$—;

$R_5$ represents an alkyl; and substituent group A comprises an alkoxyl group, an amide group, an amino group, a carbonyl group, a carboxyl group, a hydroxyl group, and a heterocyclic group.

In various embodiments, the photochromic article comprises one or more regions having a substantially reversible photoresponsive wettability that are configured for fluid manipulation. In various embodiments, the photochromic article comprises one or more regions having substantially reversible photoresponsive wettability that are configured for molecular separation. In various embodiments, the photochromic article comprises one or more regions having photoresponsive wettability that are configured for one or more of metal centered redox chemistry or heterogeneous catalysis.

In various aspects, the present invention provides methods of forming on a surface a substantially monolayer thick molecular film having a photoresponsive wettability, the method comprising the steps of:

contacting the surface of a substrate with a solution containing a organic tethering molecule, the organic tethering molecule having the general formula (III) below, $$R_2(X)_m R_3 R_4 \quad (III);$$

rinsing with a solvent and substantially drying the organic tethering molecule surface;

contacting the organic tethering molecule surface with a solution containing a metal ion M, wherein M comprises a transition metal ion of oxidation state I, II, III, IV, V, or VI, a lanthanide metal ion of oxidation state I, II, III, IV, V, or VI, or a lead ion of oxidation state IV;

rinsing with a solvent and substantially drying the M coordinated organic tethering molecule surface; and contacting the M coordinated organic tethering molecule surface with a solution containing a photochromic molecule;

wherein, $R_2$ represents an unsubstituted heterocyclic group coordinated to M, a substituted heterocyclic group coordinated to M, or a substituted aryl group coordinated to M (wherein the substituted aryl group is substituted with one or more oxygen, nitrogen or oxygen and nitrogen containing substituents from the substituent group A);

the dashed line represents the coordination of one or more donor atoms to M;

X represents a —NH—, —O—, or —S—;

m represents 0 or 1;

$R_3$ represents an alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof;

$R_4$ represents a bond, —O—, —S—, —P—, —CH$_2$—, —OSi(OR$_5$)$_2$or —OSiCl$_2$—;

$R_5$ represents an alkyl; and substituent group A comprises an alkoxyl group, an amide group, an amino group, a carbonyl group, a carboxyl group, a hydroxyl group, and a heterocyclic group.

In various embodiments, the present inventions provide films where the photoconversion between configurations of the photochromic molecule is substantially reversible by irradiation with light. In various embodiments, the present inventions provide films where the photoconversion is substantially irreversible by irradiation with light. As discussed further below, both the substantially reversible and substantially irreversible films of the present invention can have useful applications.

The foregoing and other aspects, embodiments, and features of the invention can be more fully understood from the following description in conjunction with the accompanying drawings. In the drawings like reference numerals generally refer to like features and structural elements throughout the various figures. The drawings are not necessarily to scale, emphasis instead being placed upon illustrating the principles of the invention.

DETAILED DESCRIPTION OF THE INVENTION

Figure 1:
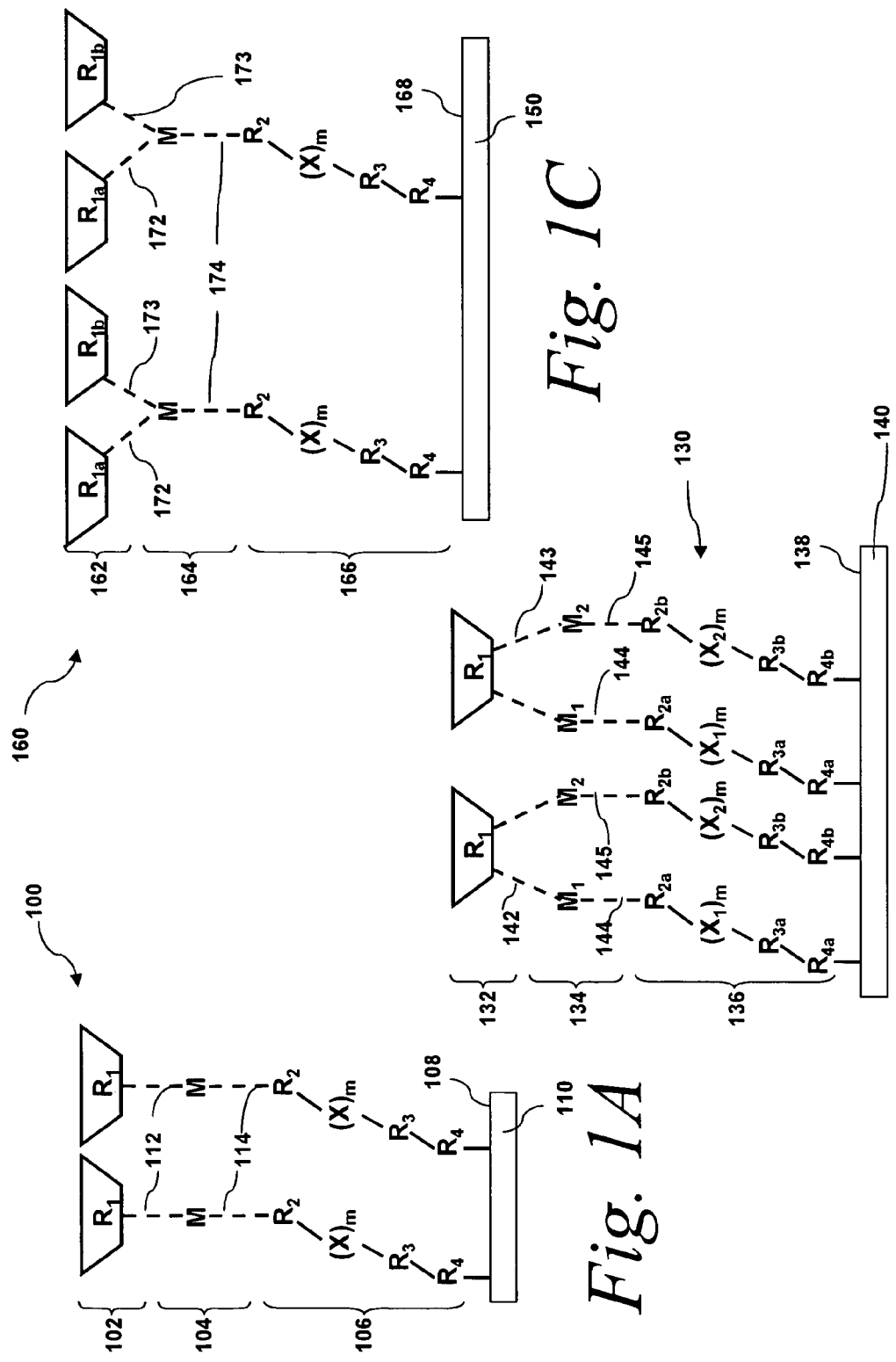
FIGS. 1A-1C schematically illustrates various embodiments of a substantially monolayer thick photochromic film of various embodiments of the present invention.

Prior to further describing the invention, it may be helpful to an understanding thereof to set forth definitions of certain terms to be used herein.

As used herein, the term "light" refers to electromagnetic radiation having at least one wavelength in the range between about 100 nanometers (nm) to about 1400 nm. The term light is not limited to coherent electromagnetic radiation (e.g., as provided by a laser) but also includes incoherent radiation (e.g., as provided by a lamp, heater, etc.). The term light includes both broadband radiation (e.g., light comprising a broad range of wavelengths, some of which may be below about 100 nm or above about 1400 nm,), multiband radiation, and narrowband radiation. As the term "light" includes the infrared portion of the electromagnetic spectrum, it is to be understood that the phrase "irradiation with light" includes heating.

Photochromism in the scientific literature is often defined as a reversible transformation of a chemical species induced in one or both directions by absorption of electromagnetic radiation between two configurations (or forms), A and B, the two configurations having different absorption spectra. The configurations of a photochromic molecule can be collectively referred to as a photochromic system.

The photochromic processes can involve a one-photon mechanism, multi-photon mechanism, or both. For example, in typical one-photon mechanisms configuration B is formed via a singlet electronic excited state of configuration A, a triplet electronic excited state of configuration A, or both. Configuration B can also be formed from an upper excited state populated by absorption of two or more photons. Typical two-photon mechanisms include, e.g.,: (i) simultaneous absorption of two photons via a virtual level; and (ii) stepwise (or sequential) two-photon absorption where the second photon absorption takes place from a real level.

As used herein, the term "photochromic molecule" refers to molecules that can exhibit photochromism in a free or solvated state. However, as used herein, the term "photochromic molecule" is not limited to molecules which exhibit a reversible transformation between configurations A and B when these molecules are coordinated by one or more donor atoms to the metal atom of a molecular film of the present invention. Accordingly, as used herein, the term "photochromic molecule" includes molecules that when coordinated by one or more donor atoms to the metal atom of a molecular film of the present invention can change from a first configuration to a second configuration upon irradiation with light but which do not substantially revert from the second configuration (e.g., configuration B) back to the first configuration (e.g., configuration A) upon irradiation with light of the same or different wavelength. Examples of photochromic molecules, as the term is used herein, include substituted and unsubstituted: spiropyrans, spirooxazines, dipyridyls, chromenes, spirodihydro-indolizines, diazenes, and combinations thereof.

Preferred photochromic molecules are those molecules that exhibit a substantial change in dipole moment between the first and second configurations of the photochromic molecule. Examples of preferred photochromic molecules include, but are not limited to, 6-nitro-1',3',3'-trimethylspiro (2H-1-benzopyran-2,2'indoline), and 2,2'-dipyridylethylene. Preferred photochromic molecules include photochromic molecules that undergo the photochromic process via a one-photon mechanism.

In addition, the term photochromic molecule includes molecules which exhibit gated photochromism. Gated photochromism is a type of photochromism in which one or more forms of the photochromic system are transformed (e.g., chemically or electrochemically) reversibly into a nonphotochromic form. The control of the photochromic process can be likened metaphorically to flow through a gate. The opening or closing of the gate can depend on external stimuli such as protonation, oxido-reduction, solvation, and temperature. The term photochromic molecule also includes molecules which may also exhibit acidichromism. Acidichromism is a type of photochromism in which the protonated form and the conjugate base of some compounds have distinctly different absorption spectra. Acidichromism can occur, e.g., for spirooxazines which generate merocyanines.

The term "substituted" is intended to describe groups having substituents replacing a hydrogen on one or more atoms, e.g., carbon, nitrogen, oxygen, etc., of a molecule. It will also be noted that the substituents of some of the compounds of this invention include isomeric structures. It is to be understood accordingly that constitutional isomers of particular substituents are included unless indicated otherwise.

Substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic group. Accordingly, the phrase "a substituents as described herein" or the like refers to one or more of the above substituents, and combinations thereof.

The term "alkyl" includes saturated aliphatic groups, which includes both "unsubstituted alkyls" and "substituted alkyls", the latter of which refers to alkyl groups having substituents replacing a hydrogen on one or more carbons of the hydrocarbon backbone. The term "alkyl" includes straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and cycloalkyl substituted alkyl groups. The term "alkyl" also includes the side chains of natural and unnatural amino acids.

An "alkylaryl" or an "aralkyl" group is an alkyl substituted with an aryl (e.g., phenylmethyl (benzyl)).

The term "aryl" includes 5- and 6-membered single-ring aromatic groups, as well as multicyclic aryl groups, e.g., tricyclic, bicyclic, e.g., naphthalene, anthracene, phenanthrene, etc.). The aromatic ring(s) can be substituted at one or more ring positions with such substituents as described above. Aryl groups can also be fused or bridged with, e.g., alicyclic or heterocyclic rings which are not aromatic so as to form, e.g., a polycycle.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl includes both "unsubstituted alkenyls" and "substituted alkenyls", the latter of which refers to alkenyl groups having substituents replacing a hydrogen on one or more carbons of the hydrocarbon backbone.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

The term "acyl" includes compounds and groups which contain the acyl radical ($CH_3CO$—) or a carbonyl group. The term "substituted acyl" includes acyl groups having substituents replacing a one or more of the hydrogen atoms.

The term "acylamino" includes groups wherein an acyl group is bonded to an amino group. For example, the term includes alkylcarbonylamino, arylcarbonylamino, carbamoyl and ureido groups.

The term "aroyl" includes compounds and groups with an aryl or heteroaromatic group bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or groups that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "carbonyl" or "carboxy" includes compounds and groups which contain a carbon connected with a double bond to an oxygen atom, and tautomeric forms thereof.

Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "ether" includes compounds or groups that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and groups that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and groups which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or groups wherein an alkyl, alkenyl, or alkynyl group is bonded to a sulfur atom which is covalently bonded to an alkynyl group.

The term "hydroxy" or "hydroxyl" includes groups with an —OH or —O—.

The term "halogen" includes fluorine, bromine, chlorine, iodine, etc. The term "perhalogenated" generally refers to a group wherein all hydrogens are replaced by halogen atoms.

The term "heteroatom" includes atoms of any element other than carbon or hydrogen. Preferred heteroatoms are nitrogen, oxygen, sulfur and phosphorus.

The term "heterocycle" or "heterocyclic" includes saturated, unsaturated, aromatic ("heteroaryls" or "heteroaromatic") and polycyclic rings which contain one or more heteroatoms. The heterocyclic may be substituted or unsubstituted. Examples of heterocyclics include, for example, benzodioxazole, benzofuran, benzoimidazole, benzothiazole, benzothiophene, benzoxazole, chromene, deazapurine, furan, indole, indolizine, imidazole, isoxazole, isoindole, isoquinoline, isothiazole, methylenedioxyphenyl, napthridine, oxazole, purine, pyran, pyrazine, pyrazole, pyridazine, pyridine, pyrimidine, pyrrole, quinoline, tetrazole, thiazole, thiophene, and triazole. Other heterocycles include morpholino, piprazine, piperidine, thiomorpholino, and thioazolidine.

The term "ORMOSIL" refers to organically modified silicates. One example of an ORMOSIL is polydimethyl siloxane (PDMS). Examples of ORMOSIL gels include gel structures of the formulae (IVa) and (IVb):

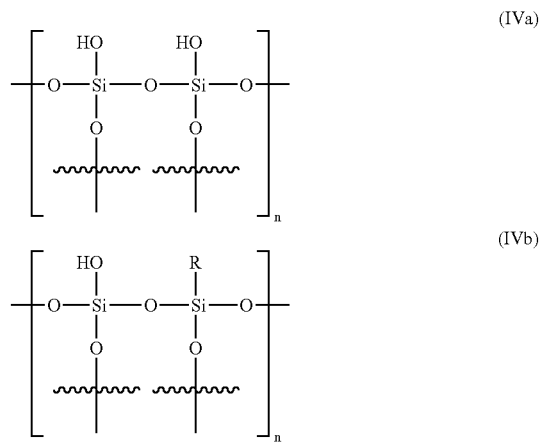

where R represents, e.g., a substituted or unsubstituted: alkyl, alkenyl, aryl, ether, heterocycle, heteroaryl, and combinations thereof. For example, in various embodiments R is a 2,6-pyridinedicarboxylate group.

The terms "polycyclyl" or "polycyclic radical" include groups with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above.

The term "thiocarbonyl" or "thiocarboxy" includes compounds and groups which contain a carbon connected with a double bond to a sulfur atom. The term "thiocarbonyl group" includes groups that are analogous to carbonyl groups. For example, "thiocarbonyl" groups include aminothiocarbonyl, wherein an amino group is bound to the carbon atom of the thiocarbonyl group, furthermore other thiocarbonyl groups include, oxythiocarbonyls (oxygen bound to the carbon atom), aminothiocarbonylamino groups, etc.

It will be noted that the structures of some of the compounds of this invention include asymmetric carbon atoms. It is to be understood accordingly that the isomers arising from such asymmetry (e.g., all enantiomers and diastereomers) are included within the scope of this invention, unless indicated otherwise. Furthermore, the structures and other compounds, groups and groups discussed in this application also include all tautomers thereof.

Additionally, the phrase "and combination thereof" implies that any number of the listed functional groups and molecules may be combined to create a larger molecular architecture. For example, the terms "pyridine," two "carbonyl" (or "C=O"), and two "—OH," (or, e.g, two carboxylates —COOH) can be combined to form a dicarboxypyridine substituent. It is to be understood that when combining functional groups and molecules to create a larger molecular architecture, hydrogens can be removed or added as required to satisfy the valence of each atom.

Monolayers with Photoresponsive Wettability

In various aspects, the present invention provides a substantially monolayer thick molecular film having photoresponsive wettability. The photoresponsive wettability of the films is provided by the photochromic molecular surface of the film. Specifically, in various embodiments, the present invention provides films where irradiation of the film with a first wavelength of light photoconverts the photochromic molecules in the irradiated portions of the film from a first configuration to a second configuration. The second configuration providing a surface with a wettability different than that provided by the first configuration.

In preferred embodiments, one configuration of the photochromic molecule provides a surface with a hydrophobic surface and another configuration of the photochromic molecule provides a surface with a hydrophilic surface. In preferred embodiments, the change in contact angle for water on the surface, between the first and second configurations is greater than about 10°, and more preferably greater than about 15°.

Schematic examples of various embodiments of the substantially monolayer thick molecular films of the present invention are illustrated in FIGS. 1A-1C and FIGS. 2A-2C. The graphical structures depicted in FIGS. 1A-1C and 2A-2C are provide for illustrative purposes only and are not intended to be limiting. Referring to FIGS. 1A-1C, various examples of the units of a molecular film 100, 130, 160 comprising molecules of a general formula,

$$R_1\text{-}M\text{-}R_2(X)_m R_3 R_4 \quad (I),$$

are illustrated. In various embodiments, the molecular films comprise a photochromic molecule component (e.g., $R_1$ $R_{1a}$, $R_{1b}$) 102, 132, 162, a metal atom component (e.g., M, $M_1$, $M_2$) 104, 134, 164, and an organic tethering molecule component (e.g., collectively $R_2(X)_m R_3 R_4$) 106, 136, 166 attaching the film to the surface 108, 138, 168 of a substrate 110, 140, 170. Preferably, the organic tethering molecule component 106, 136, 166 comprises one or more self assembling molecules that when contacted with the surface 108, 138, 168 of the substrate 110, 140, 170 form a self assembled monolayer on the surface 108, 138, 168.

Various examples of the complexation of photochromic molecules to the metal atoms are shown, including 1:1 metal:photochromic molecule complexes (FIG. 1A); 2:1 metal:photochromic molecule complexes (FIG. 1B); and 1:2 metal:photochromic molecule complexes (FIG. 1C). In various embodiments, even higher order (e.g. 3:1, 1:3, etc.) metal:photochromic molecule complexes can form. The photochromic molecules can be monodentate or multidentate ligands of a given metal atom. Thus, it is to be understood that the metal-ligand bonds 112, 114, 142, 143, 144, 145, 172, 173, 174 are illustrated by a single dashed line for ease of representation only. The number of metal-ligand bonds between the photochromic molecule (e.g., $R_1$ $R_{1a}$, $R_{1b}$) and metal atom (e.g., M, $M_1$, $M_2$) depend, for example, on the oxidation state of the metal atom M, the nature of the donor atoms (one electron, two electron, three electron, etc.) and the number of metal-ligand bonds between the metal atom M and a "head group" (e.g., $R_2$, $R_{2a}$, $R_{2b}$) of the organic tethering molecule.

In various embodiments of a 2:1 metal:photochromic molecule complex (FIG. 1B) the metal atoms ($M_1$, $M_2$) can be different metals, the same metal with different oxidation states, or both. In various embodiments, one or more of the groups comprising the organic tethering molecules ($R_{2a}$ $(X_1)_m R_{3a} R_{4a}$ and $R_{2b}(X_2)_m R_{3b} R_{4b}$) can independently be the same, or different. In various embodiments of a 2:1 metal:photochromic molecule complex (FIG. 1C), the photochromic molecules ($R_{1a}$, $R_{1b}$) can be different photochromic molecules, different configurations of molecules of a photochromic system or both.

The "head group" (e.g., $R_2$, $R_{2a}$, $R_{2b}$) of the organic tethering molecule can be a monodentate or multidentate ligand of a given metal atom. Referring to FIG. 3, in various embodiments, films 300 can be formed where the "head group" (e.g., $R_{2a}$, $R_{2b}$) of the organic tethering molecule component 302, forms higher order metal:head group complexes (e.g., 1:2, 1:3, etc.; a 1:2 complex is illustrated) with the metal atom component 304. Although the photochromic molecule component is not shown in FIG. 3, any of the coordination arrangements of the photochromic molecule component with the metal atom of FIGS. 1A-1C and FIGS. 2A-2C can be used with the metal atom organic tethering molecule component arrangements of FIG. 3.

Figure 2:
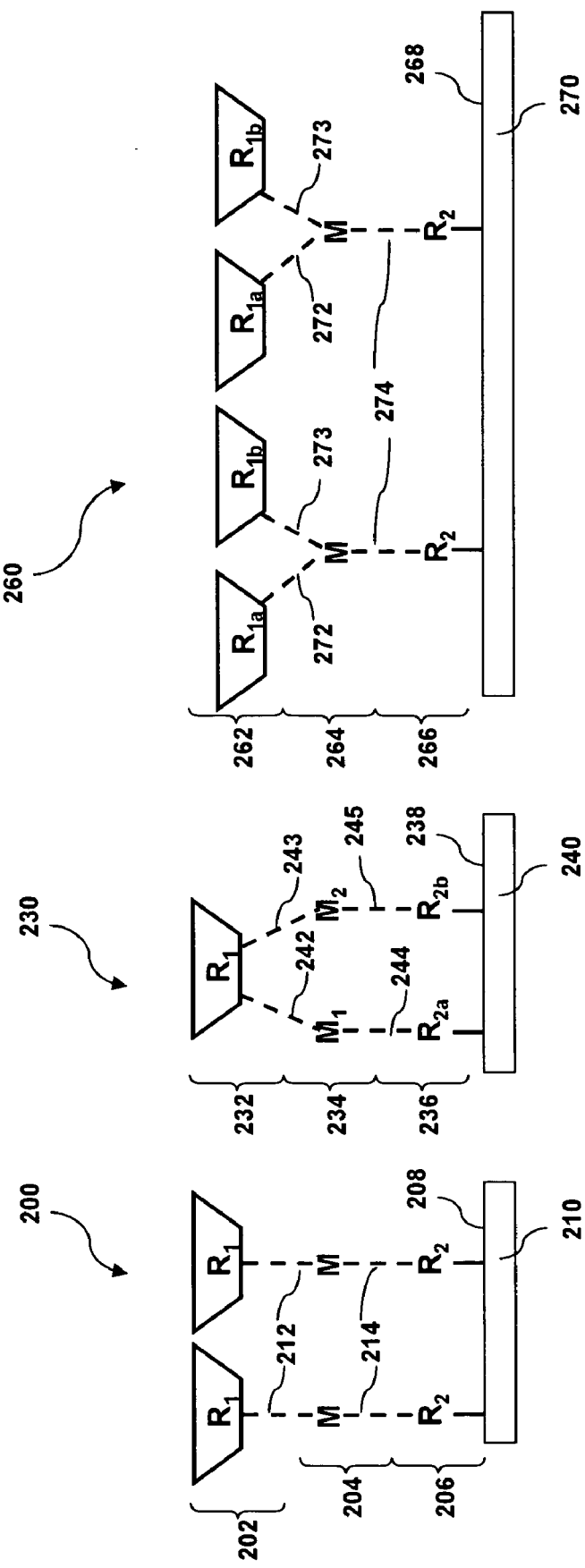
FIGS. 2A-2C schematically illustrates various embodiments of a substantially monolayer thick photochromic film of various embodiments of the present invention.
Figure 3:
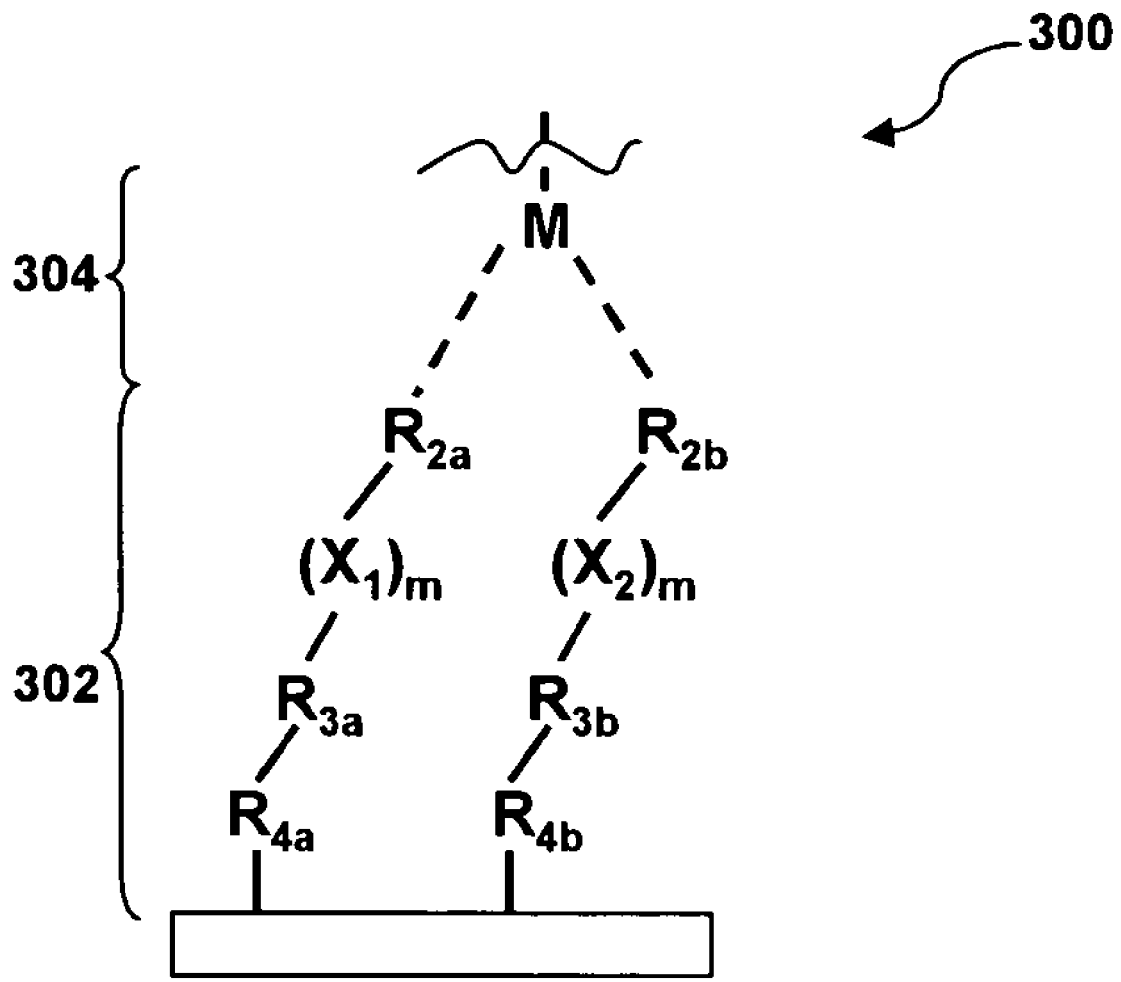
FIG. 3 schematically illustrates various embodiments of the binding of the metal atoms to one or more organic tethering molecules.

Referring to FIGS. 2A-2C, various examples of the units of a molecular film 200, 230, 260 comprising molecules of a general formula,

$$R_1\text{-}M\text{-}R_2 \quad (II),$$

are illustrated. In various embodiments, the molecular films comprise a photochromic molecule component (e.g., $R_1$ $R_{1a}$, $R_{1b}$) 202, 232, 262, a metal atom component (e.g., M, $M_1$, $M_2$) 204, 234, 264, and a coupling group component (e.g., $R_2$, $R_{2a}$, $R_{2b}$) 206, 236, 266 attaching the film to the surface 208, 238, 268 of a substrate 210, 240, 270 wherein, the substrate surface 208, 238, 268 comprises one or more of a polymer, plastic, or ORMOSIL gel.

In preferred embodiments, the coupling group component (e.g., $R_2$, $R_{2a}$, $R_{2b}$) comprises one or more of: —OR, —SH, —NH$_2$, —SO$_2$OR, —PO(OR)(OR'), -carboxylates, substituted pyridines, unsubstituted imidazoles, substituted imidazoles,

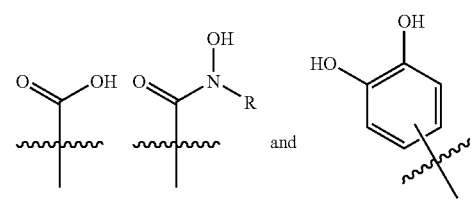

where R and R' independently represent a hydrogen, or a substituent as described herein.

Various examples of the complexation of photochromic molecules to the metal atoms are shown, including 1:1 metal:photochromic molecule complexes (FIG. 2A); 2:1 metal:photochromic molecule complexes (FIG. 2B); and 1:2 metal:photochromic molecule complexes (FIG. 2C). In various embodiments, even higher order (e.g. 3:1, 1:3, etc.) metal:photochromic molecule complexes can form. The photochromic molecules can be monodentate or multidentate ligands of a given metal atom. Thus, it is to be understood that the metal-ligand bonds 212, 214, 242, 243, 244, 245, 272, 273, 274 are illustrated by a single dashed line for ease of representation only. The number of metal-ligand bonds between the photochromic molecule (e.g., $R_1$ $R_{1a}$, $R_{1b}$) and metal atom (e.g., M, $M_1$, $M_2$) depend, for example, on the oxidation state of the metal atom M, the nature of the donor atoms (one electron, two electron, three electron, etc.) and the number of metal-ligand bonds between the metal atom M and coupling group (e.g., $R_2$, $R_{2a}$, $R_{2b}$).

In various embodiments of a 2:1 metal:photochromic molecule complex (FIG. 2B) the metal atoms ($M_1$, $M_2$) can be different metals, the same metal with different oxidation states, or both. In various embodiments, one or more of the coupling group (e.g., $R_2$, $R_{2a}$, $R_{2b}$) can be the same, or different. In various embodiments of a 2:1 metal:photochromic molecule complex (FIG. 2C) the photochromic molecules ($R_{1a}$, $R_{1b}$) can be different photochromic molecules, different configurations of molecules of a photochromic system or both.

The thickness of the films of the present invention, over the region of interest on a substrate, is believed, without being held to theory, to be important as a substantially uniform surface can be provided by a substantially monolayer thick film of the present invention. Thus, areas of relatively well defined wettability can be provided, which facilitate, for example, the use of the films of the present inventions in micro- and nanofluidic devices. In addition, in various embodiments, the substantially monolayer thickness of the films can provide photochromic articles (e.g., beads or other structures coated with a molecular film of the present invention) having a relatively large surface area to volume ratio. The photoresponsive wettability of, e.g., such photochromic articles, in various embodiments, can facilitate providing surfaces for redox chemistry, catalysis chemistry, etc. that can be controlled by, initiated by, terminated by, modultated by, etc. (or in general responsive to) irradiation with light.

A variety of techniques exist to assess the properties of a film on a surface, e.g., grazing-angle Fourier transform infrared spectroscopy (grazing-angle FT-IR), quartz crystal gravimetry, atomic force microscopy (AFM), scanning electron microscopy (SEM), cyclic voltametry, contact angle measurements, and ellipsometry. For example, AFM and ellipsometry can give a relatively direct measure of the thickness of a film. AFM and ellipsometry are preferred methods for determining the thickness of the molecular films of the present invention, and a region of a film is considered to be a monolayer thick if one or more of these AFM and ellipsometry methods indicate that the film is a monolayer thick to a reasonable degree of certainty.

Photochromic Molecule Component

As discussed above, the photoresponsive wettability of the photochromic molecular films of the present inventions can be provided by the photochromic molecular surface of the film. Specifically, in various embodiments, the present invention provides molecular films where irradiation of the film with a first wavelength of light photoconverts the photochromic molecules in the irradiated portions of the film from a first configuration to a second configuration. The second configuration providing a surface with a wettability different than that provided by the first configuration.

Photochromic molecules suitable for use in various embodiments, e.g., of formulae (I), (II), (VI), (VII), and (VIII) include spiropyrans, spirooxazines, dipyridyls, chromenes, spirodihydro-indolizines, diazenes, and combinations thereof. Examples of photochromic transitions for these classes of photochromic molecules are illustrated in FIGS. 4A-4E, where $hv_1$ is less than $hv_2$ in all cases. In FIGS. 4A-4E only one molecule of each class is shown for illustrative purposes only and not by way of limitation. In addition, the molecule shown may be a substituted member of the class.

Figure 4A:
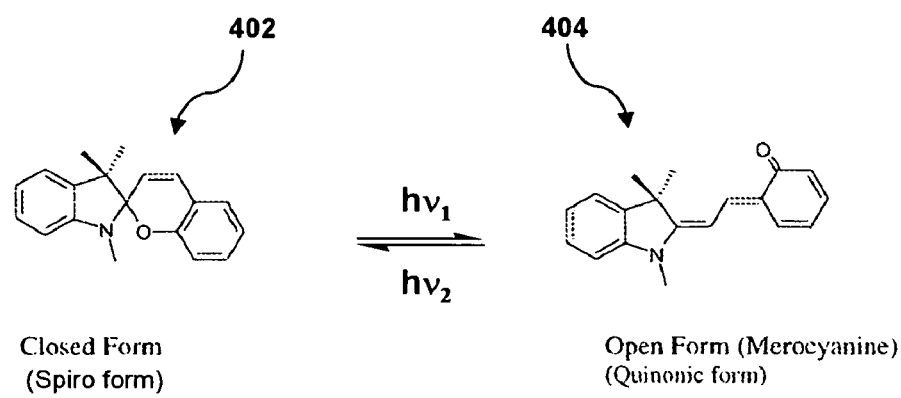
FIGS. 4A-4E schematically illustrates examples of various families of photochromic molecules suitable for use in various embodiments in the present invention.
Figure 4B:
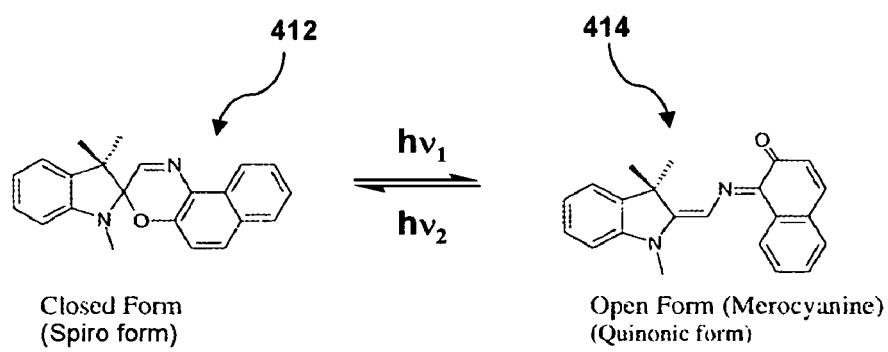
Figure 4C:
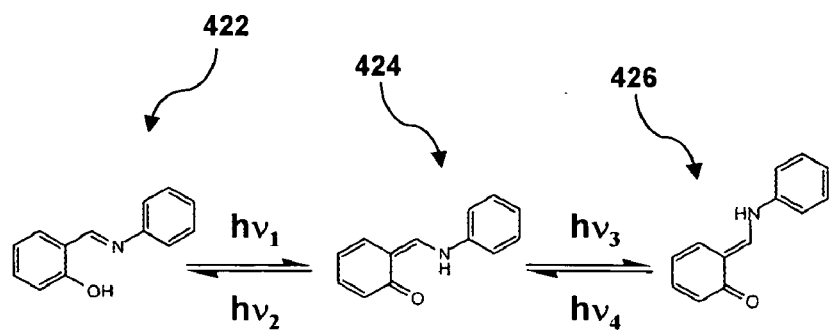
Figure 4D:
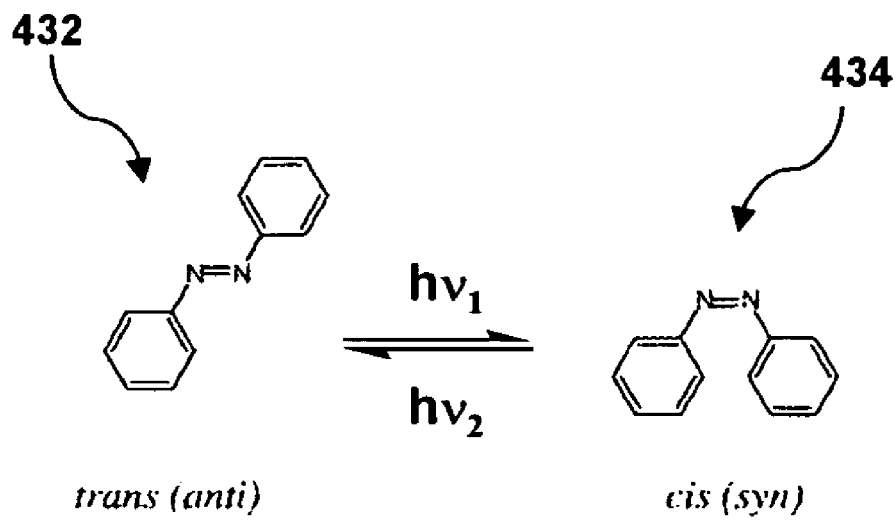
Figure 4E:
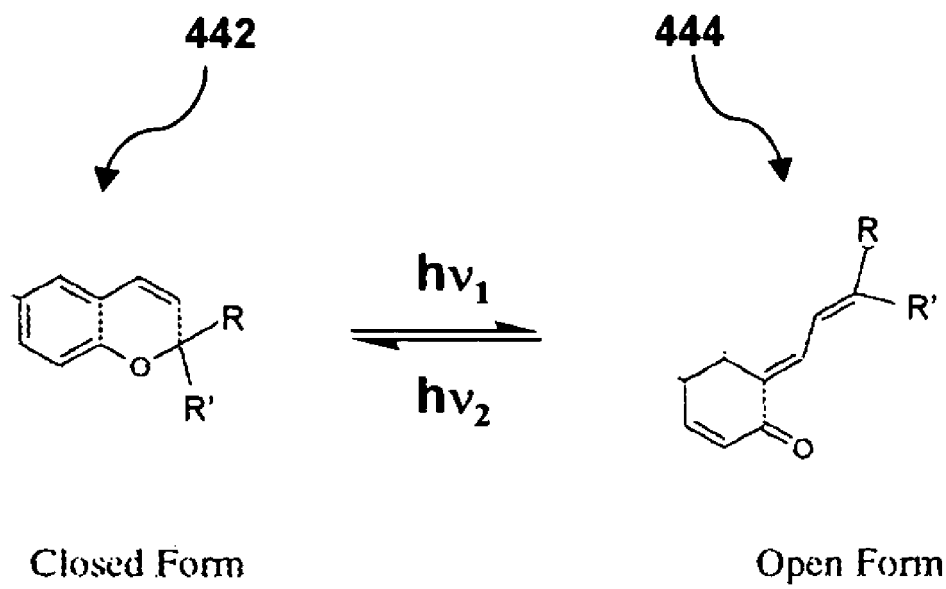

FIG. 4A depicts a photochromic transition of a spiropyran from the closed spiro form 402 to the open merocyannie form 404, the quinoinic structure is illustrated but it is to be understood that a zwitterionic structure can exist. FIG. 4B depicts a photochromic transition of a spirooxazine from the closed spiro form 412 to the open merocyannie form 414, the quinoinic structure is illustrated but it is to be understood that a zwitterionic structure can exist. FIG. 4C depicts a photochromic transition of an anil 422 involving a hydrogen transfer, two isomers 424, 426 are shown which form part of the photochromic system. FIG. 4D depicts a photochromic transition of an azo compound from a trans isomer 432 to a cis isomer 434. FIG. 4E depicts a photochromic transition of chromene from a closed form 442 to an open form 444.

Changes in wettability can arise from one or more changes in the surface properties of the molecular films of the present invention. For example, changes in wettability can arise from changes in dipole moment between configurations of the photochromic molecules, thus leading, e.g., to changes in surface free energy and wettability. Changes in dipole moment can arise from a number of process including, for example, isomerization (e.g., cis-trans isomerization), electron transfer, intramolecular hydrogen transfer, intramolecular group transfer, pericyclic reactions (e.g., electrocyclizations, and cycloadditions), and dissociation processes. Multiple processes can occur in a single photo conversion.

Processes that change charge localization within the photochromic molecule can have a particular impact on the dipole moment. For example, the merocyanine configurations of spiropyrans and spirooxazines can have zwitterion structures. Such structures can have substantially different dipole moments from the corresponding spiropyran or spirooxazine member of the photochromic system.

In addition to dipole moment changes, changes in the coordination of the photochromic molecule to the metal atom, M, (arising, e.g., from conformational changes and/or rearrangements of the photochromic molecule) can result in increased or decreased ability of the metal atoms to interact with substances on the surface of the film. For example, referring to FIG. 5A, the substantially monolayer thick molecular film comprising a photochromic molecule component 501, a metal atom component 502, and a organic tethering molecule component 503, attached to the surface 504 of a substrate 505 via a surface coupling group 506. In a first configuration the photochromic molecule 508, the cis form of 2,2'-dipyridylethylene, serves as a bidentate ligand for the metal atom (Cu(II)) and provides a highly hydrophobic (poorly wetting) surface 512. Upon exposure of the film to 300 nm light, the dipyridylethylene undergoes a cis-trans isomerization, to the trans configuration 514 and the photochromic molecule becomes a substantially monodentate ligand, of the metal atom which serves to expose the underlying metal ion and significantly enhances the hydrophilicity, and wetting properties, of the molecular film surface 518.

Figure 5A:
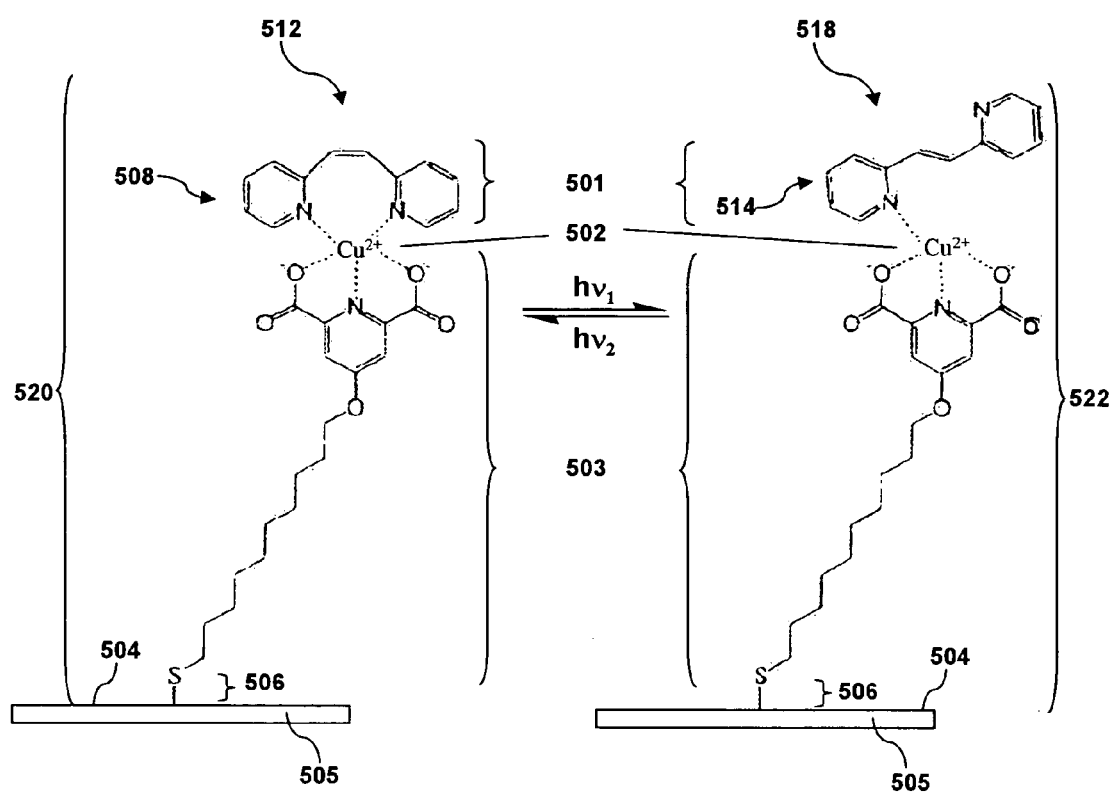
FIGS. 5A and 5B schematically illustrate various embodiments of a substantially monolayer thick photochromic film having a photoresponsive wettability.
Figure 5B:
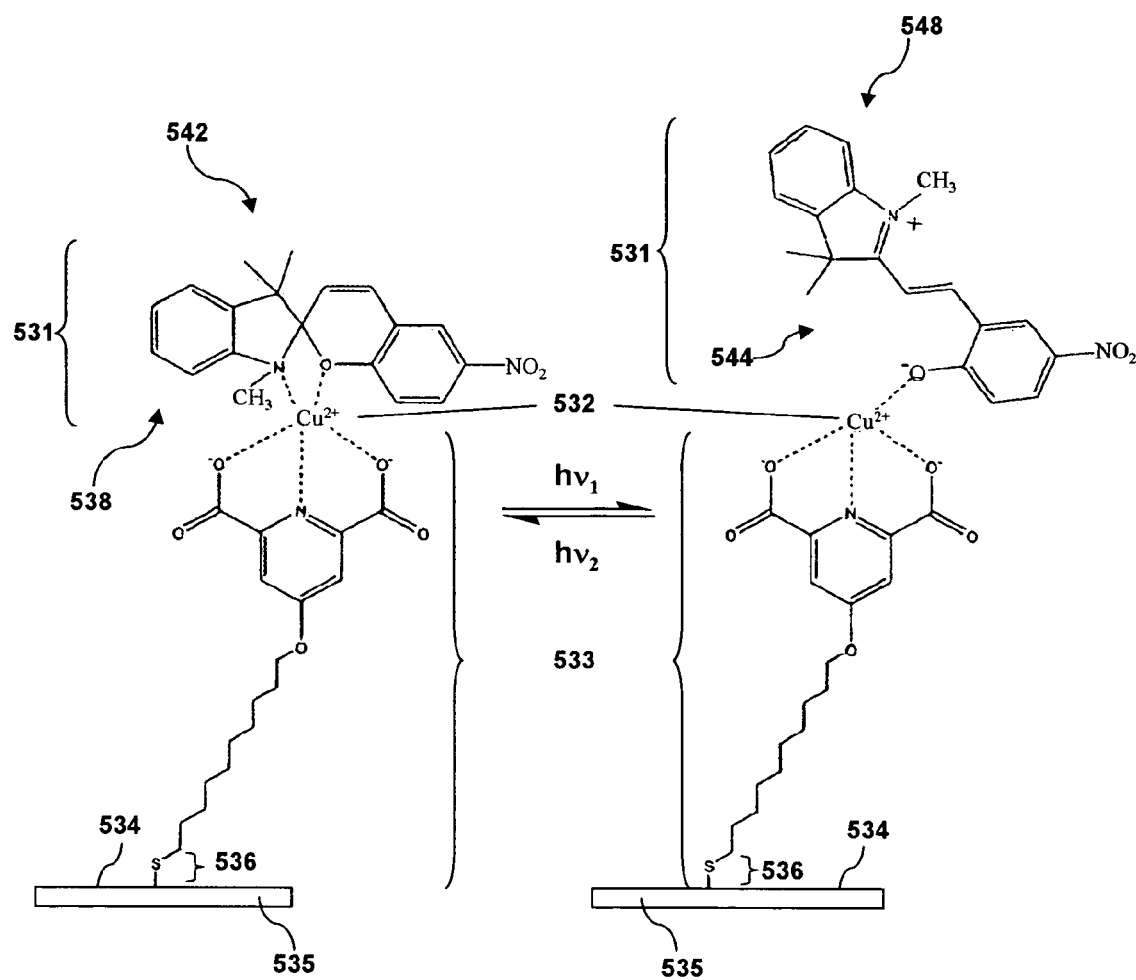

Another example is provided by FIG. 5B, the substantially monolayer thick molecular film comprising a photochromic molecule component 531, a metal atom component 532, and a organic tethering molecule component 533, attached to the surface 534 of a substrate 535 via a surface coupling group 536, where in a first configuration the photochromic molecule 538, the spiropyran form of 6-nitro-1',3',3'-trimethylspiro (2H-1-benzopyran-2,2'indoline), serves as a bidentate ligand for the metal atom (Cu(II)) and provides a hydrophobic (poorly wetting) surface 542. Upon exposure of the film to UV radiation (e.g., 300 nm light), the spiropyran opens to the merocyanine form 544, to become a substantially monodentate ligand, which serves to expose the underlying metal ion, and which can exist as a zwitterion, significantly enhancing the hydrophilicity and wetting properties, of the molecular film surface 548.

The spiropyran configuration of 6-nitro-1',3',3'-trimethylspiro (2H-1-benzopyran-2,2'indoline) is a colorless, UV absorbing molecule while the merocyanine configuration is highly colored with an absorption band typically in the 500-600 nm region. The merocyanine configuration is depicted in FIG. 5B in the all-trans form although a cis-isomer is also known. In the ground state, an equilibrium exists between the two configurations with the equilibrium usually strongly favoring the spiropyran form.

Spiropyran compounds and spirooxazines are photochromic in that exposure of the spiropyran configuration to UV light can cause a transformation to the merocyanine configuration, while exposure of the merocyanine configuration to visible wavelengths of light can cause reversion to the spiropyran configuration. The spiropyran and spirooxazine photochromic systems can be deposited as photochromic molecules in the spiropyran and the merocyanine configurations since, for example, there are donor atoms, e.g., oxygen and nitrogen, suitable for coordination with the metal atom, in both configurations. Further suitable donor atoms can be provided, for example, by substitution of the 8 position with group containing an oxygen and/or nitrogen containing group, such as, for example, an amide, an alkoxy, a carbonyl, a carboxylate, a alkylcarbonyl, alkylcarbonyloxy, heterocyclic, etc.

The position numbering used herein for a spiropyran or spirooxazine is shown below.

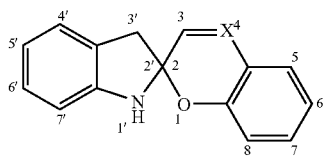

X = carbon for a spiropyran;
X = oxygen for a spirooxazine.

The identities of R (at the 8 position) and R' (at the 1' position) in a benzo indolino pyrano spiran (such as, for example derivatives of 1',3',3'-trimethylspiro (2H-1-benzopyran-2,2'indoline)) can have an effect on the formation of complexes. Bulky groups on the nitrogen atom (R') can potentially prevent coordination of the spiropyran configuration through the nitrogen of the furan. In various embodiments, the photochromic molecule comprises a 6-nitro-1', 3',3'-trimethylspiro (2H-1-benzopyran-2,2'indoline) or 1',3', 3'-trimethylspiro (2H-1-benzopyran-2,2'indoline) substituted at the 8 position with a group R, and the 1' position with group R'; where R is methoxy, ethoxy, n-propoxy, or carboxylate, and R' is methyl, ethyl, n-propyl, n-butyl, carboxylate, or a carboylate at the end of a $C_0$-$C_{10}$ alkyl chain. In various embodiments, the photochromic molecule comprises a 6-nitro-1',3',3'-trimethylspiro (2H-1-benzopyran-2,2'indoline) substituted with an aromatic ring at the 4,5; 5,6 or 6,7 positions.

The metal atom to which a spiropyran or merocyanine configuration of a spiropyran or spirooxazine is coordinated can also effect the equilibrium between the two forms. For example, coordination of 6-nitro-1',3',3'-trimethylspiro (2H-1-benzopyran-2,2'indoline) to a lanthanide metal typically shifts the equilibrium from the spiropyran to the merocyanine configuration. This complex formation is accompanied by a blue-shift in the absorption spectrum of the merocyanine form.

Metal Atom Component

A wide variety of metals, and oxidation states thereof, can be used in the substantially monolayer thick molecular films of the present invention. In general, the metal atom provides a means to non-covalently link the functionality of the photochromic molecule to an organic tethering molecule, coupling group, or both. Preferably, the organic tethering molecule, coupling group, or both, form a self-assembled monolayer on the surface of a substrate to be coated.

Suitable metal atoms for the metal atom component include transition metals having oxidation states of I, II, III, IV, V, or VI, lanthanide metals having oxidation states of I, II, III, IV, V, or VI, and lead (Pb) having an oxidation state of IV. For example, first row transition metals, such as titanium (Ti), vanadium (V), chromium (Cr), manganese (Mn), iron (Fe), cobolt (Co), nickel (NI), copper (Cu) and zinc (Zn) can be used. Examples of preferred oxidation state two metal atoms include Mn(II), Co(II), Cu(II), and Zn (II). In various embodiments, metal atoms with oxidation states that form substantially octohedral complexes are preferred, for example, to provide better packing. Examples of preferred oxidation state three metal atoms include Fe(III), and examples of preferred oxidation state four metal atoms include Ti (IV) and Pb(IV).

Organic Tethering Molecule Components and Coupling Groups

The organic tethering molecule component preferably comprises a molecule capable of forming a self-assembled monolayer on the surface of the substrate to be coated with a film of the present invention. In various aspects of the present invention, the films comprise an organic tethering molecule component of general formula (V) below,

$$R_2(X)_m R_3 R_4 \qquad (V).$$

The "head group" $R_2$ preferably comprises a heterocyclic or substituted aryl group comprising one or more oxygen atoms, nitrogen atoms, or both, which can coordinate to the metal atom. Examples of preferred "head groups" $R_2$ include substituted and unsubstituted: furans, imidazoles, pyrimidines, pyrroles, dicarboxypyridines (preferably 1,3 dicarboxypyridines), dicarboxybenzenes (preferably 1,3 dicarboxybenzenes), oxazines (preferably 1,3 oxazines), dicarboxyfurans (preferably 2,5 dicarboxyfurans), dicarboxypyrroles (preferably 2,5 dicarboxypyrroles), diaminepyridines (preferably 1,3 diaminepyridines), diaminebenzenes (preferably 1,3 diaminebenzenes), diaminefurans (preferably 2,5 diaminefurans), diaminepyrroles (preferably 2,5 diaminepyrroles), amino-carboxypyridines (preferably 1,3 and 3,1 aminocarboxypyridines), amino-carboxybenzenes (preferably 1,3 and 3,1 aminocarboxybenzenes), amino-carboxyfurans (preferably 2,5 and 5,2 aminocarboxyfurans), and amino-carboxypyrroles (preferably 2,5 and 5,2 aminocarboxypyrroles).

In various embodiments, the "head group" $R_2$ comprises one or more of a primary amine, a thiol alcohol, a phosphate, a phosphonate, a sulfonate, any oxygen, nitrogen, sulfur, or phosphorous containing substituents as described herein, and combinations thereof.

The $R_3$ can comprise a wide variety of compounds and groups. Preferably, $R_3$ is chosen such that its absorption of light, if any, does not detrimentally interfere with the photochromic transition of interest (typically a forward reaction, but not typically a back reaction or reaction that occur thermally) of the photochromic molecule, or molecules, of the molecular film. For example, conjugated molecules can have absorption peaks in regions in which photochromic transitions commonly occur, and in various embodiments are not preferred. In addition, in various embodiments, $R_3$ is preferably chosen to facilitate increasing the packing of metal atoms, and/or photochromic molecules on the surface. Preferred $R_3$ groups comprise a substituted or unsubstituted $C_1$-$C_{20}$ alkyl group, or a substituted or unsubstituted $C_1$-$C_{20}$ alkyl group wherein one or more of the carbon atoms of the alkyl backbone are replace with one or more of oxygen, nitrogen, sulfur, and phosphorous, a peptide chain (e.g., a helical peptide chain), and combinations thereof.

Examples of preferred "tail portions" (collectively $R_3R_4$) include alkanethiolates for gold surfaces (a sulfur atom serving as a surface coupling group); and alkane-phosphonates for GaAs and GaN surfaces (a phosphorous atom serving as a surface coupling group); and $SiX_3$ or $Si(OR)_3$ for glass, ORMOSIL gel, and metal oxide surfaces, where X=Cl, Br, or I, and R=alkyl. In general, for non-oxidized metals (e.g., gold, silver, platinum, etc.), organic tethering components can be deposited through the formation of dative bonds between the metal atoms on the surface and thiol or disulfide groups in the molecules to be deposited.

Other important classes of surfaces include alumina, glass ($SiO_2$), silicon, and ORMOSIL surfaces. Coupling groups can be formed on such surfaces by chemical modification to form —$OSiCl_2$—. For example, for polydimethyl siloxane (PDMS) substrates chemical surface modification can be achieved by forming siloxane linkages between the chemical layer deposited and Si—OH bonds on the PDMS surface (which can be created by base or oxidation treatment). Siloxane linkages can be created, e.g., by the reaction of trichlorosilyl- or trialkoxysilyl-functionalized molecules with the surface Si—OH groups. This siloxane chemistry operates with nearly any surface-bound hydroxyl group and is therefore also applicable to a wide range of metal oxide substrates, including the alumina surfaces. Chemical modification of silicon surfaces for attachment of organic molecules is well known and can be used if silicon surfaces are to be coated.

Monolayers with Substantially Reversible Photoresponsive Wettability

In various embodiments, the present invention provides molecular films where the photoconversion between configurations of the photochromic molecule is substantially reversible by irradiation with light. Examples of photochromic molecules that, in various embodiments, can provide substantially reversible photoresponsive wettability include, spiropyrans, spirooxazines, and substituted stilbenes. Substantially monolayer thick molecular films with substantially reversible photoresponsive wettability can be achieved in several ways. In various embodiments, substantially reversible photoresponsive wettability can be achieved through photoinduced interconversion between two or more members of a photochromic system where the interconverted configurations remain bound on the surface of the film. Substantially reversible photoresponsive wettability can also be achieved through photoinduced interconversion between two or more members of a photochromic system where one of the configurations detaches from the surface.

SPIROPYRAN EXAMPLE

In various embodiments, a substantially monolayer thick molecular film with a substantially reversible photoresponsive wettability can be prepared of the general formula $$R_1\text{-}M\text{-}R_2R_3R_4 \qquad (V),$$

where the head group $R_2$ is a dicarboxypyridine, $R_3$ is a $C_{11}$-$C_{16}$ alkyl group, and $R_4$ is chosen based on the substrate to which the film is to be attached, e.g., a thiol group when the substrate is a gold surface. The metal ion is Cu(II) and the photochromic molecule $R_1$ is 6-nitro-1',3',3'-trimethylspiro (2H-1-benzopyran-2,2'indoline) which can be deposited from an appropriate solvent (such as ethanol) onto the metal ions, for example, such that once deposited one or more nitrogen and/or oxygen atoms complex with the Cu(II) ion. One of many embodiments of such a film is illustrated in FIG. 5B.

The surface wettability of this film can be switched by photochemically converting the spiropyran configuration of the photochromic molecule to the merocyanine configuration by excitation in the UV region of the spectrum (e.g., with a 300 nm Rayonet lamp). The merocyanine configuration of 6-nitro-1',3',3'-trimethylspiro (2H-1-benzopyran-2,2'indoline) absorbs in the visible region, most strongly above 500 nm. Conversion of the merocyanine configuration back to the spiropyran configuration can be achieved, for example, by irradiating the merocyanine form with light in the 500-600 nm region of the spectrum (e.g., with a xenon lamp that is shone through an optical filter having substantially transmission only in this region of the spectrum).

Figure 6A:
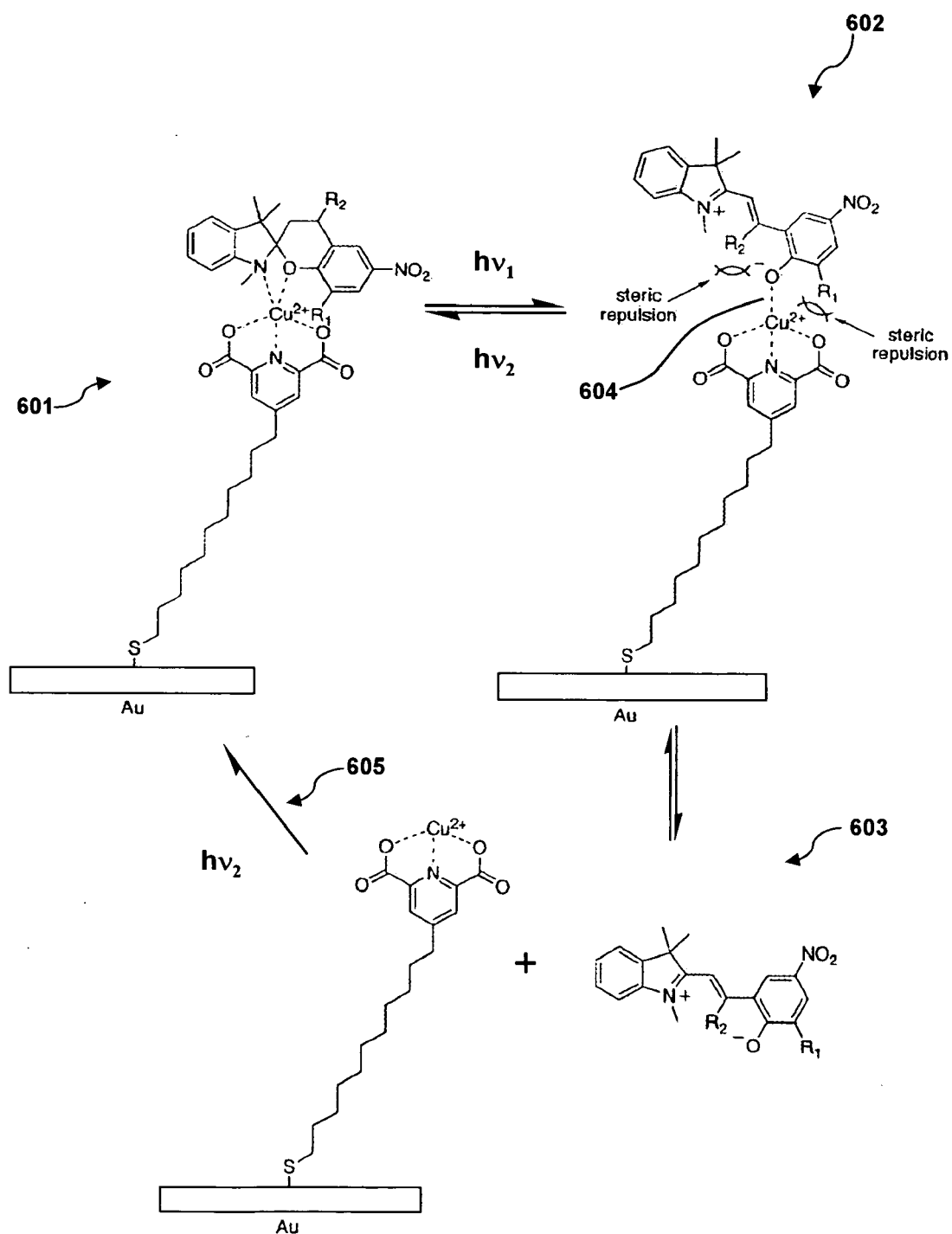
FIGS. 6A-6B schematically illustrate various embodiments of a substantially monolayer thick photochromic film with a substituted (2H-1-benzopyran-2,2'indoline) as the photochromic molecule, where the photoresponsive wettability is substantially reversible.

Substantially reversible photoresponsive wettability can also be achieved through photoinduced interconversion of a substituted spiropyran to the corresponding merocyanine where the merocyanine units detach from the surface to expose the underlying metal ions. Detachment of merocyanine units can be achieved, for example, by enhancing steric repulsion between the merocyanine units and the underlying surface. For example, referring to FIG. 6A, in various embodiments, substituents $R_1$ and $R_2$ can be placed on spiropyran at the positions indicated. Preferably, $R_1$ is an alkyl, aryl or halogen small enough to allow the spiropyran configuration to bind to the metal atom (Cu(II) in FIG. 5B), but large enough to introduce some steric repulsion relative to unsubstituted spiropyran. Preferably, $R_2$ is a large bulky alkyl, aryl or halogen. Prior to irradiation 601, $R_2$ is oriented away from the binding site with the metal atom and does not significantly interfere sterically with the binding of the spiropyran configuration to the metal. Photoinduced conversion of the spiropyran to the merocyanine 602, however, causes $R_2$ to reorient closer to the metal atom capped surface thereby increasing steric repulsion between merocyanine and the underlying metal atom capped surface. The merocyanine units can detach 603 from the metal atom when e.g., the combined steric repulsion from $R_1$ and $R_2$ becomes large enough to break the phenolate-metal bond 604. The resulting exposure of the underlying metal ions results in a more hydrophilic surface with greater wettability. Photoinduced conversion (e.g., via irradiation with light with a wavelength in the range between 500 nm to 600 nm) 605 of the merocyanine back to the spiropyran configuration reduces steric repulsion and promotes reattachment of the spiropyran units to the metal atoms.

Figure 6B:
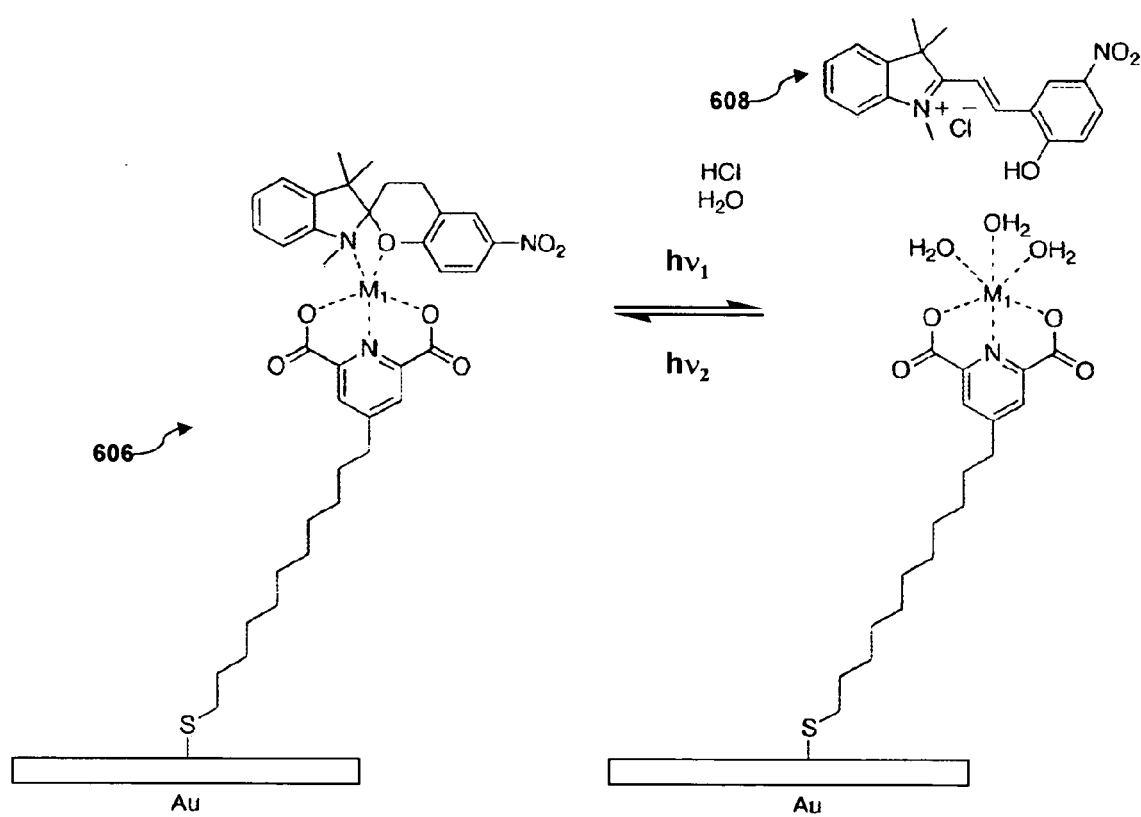

Referring to FIG. 6B, removal of merocyanine groups from the surface can also be promoted by carrying out photoconversion from spiropyran to merocyanine in the presence of a dilute aqueous acid. Conversion of the illustrated spiropyran configuration 606 can result in merocyanine units bound to the surface by a single phenolate-metal bond. Protonation of the phenolate oxygen by an acid to form a neutral hydroxyl group (OH) promotes detachment of the weakly bound merocyanine units from the metal atom. Conversion of the free merocyanine 608 back to spiropyran promotes reattachment of spiropyran units to the metal atoms.

2,2'-DIPYRIDYLETHYLENE EXAMPLE

In various embodiments, a substantially monolayer thick molecular film with a substantially reversible photoresponsive wettability can be prepared of the general formula $$R_1\text{-}M\text{-}R_2R_3R_4 \quad (VII),$$

where the head group $R_2$ is a dicarboxypyridine, $R_3$ is a $C_{11}$-$C_{16}$ alkyl group, and $R_4$ is chosen based on the substrate to which the film is to be attached, e.g., a thiol group when the substrate is a gold surface. The metal ion is Cu(II) and the photochromic molecule $R_1$ is cis-2,2'-dipyridylethylene, which can be deposited from an appropriate solvent (such as ethanol) onto the metal ions, for example, such that once deposited one or more nitrogen and/or oxygen atoms complex with the Cu(II) ion. One of many embodiments of such a film is illustrated in FIG. 5A.

Figure 7:
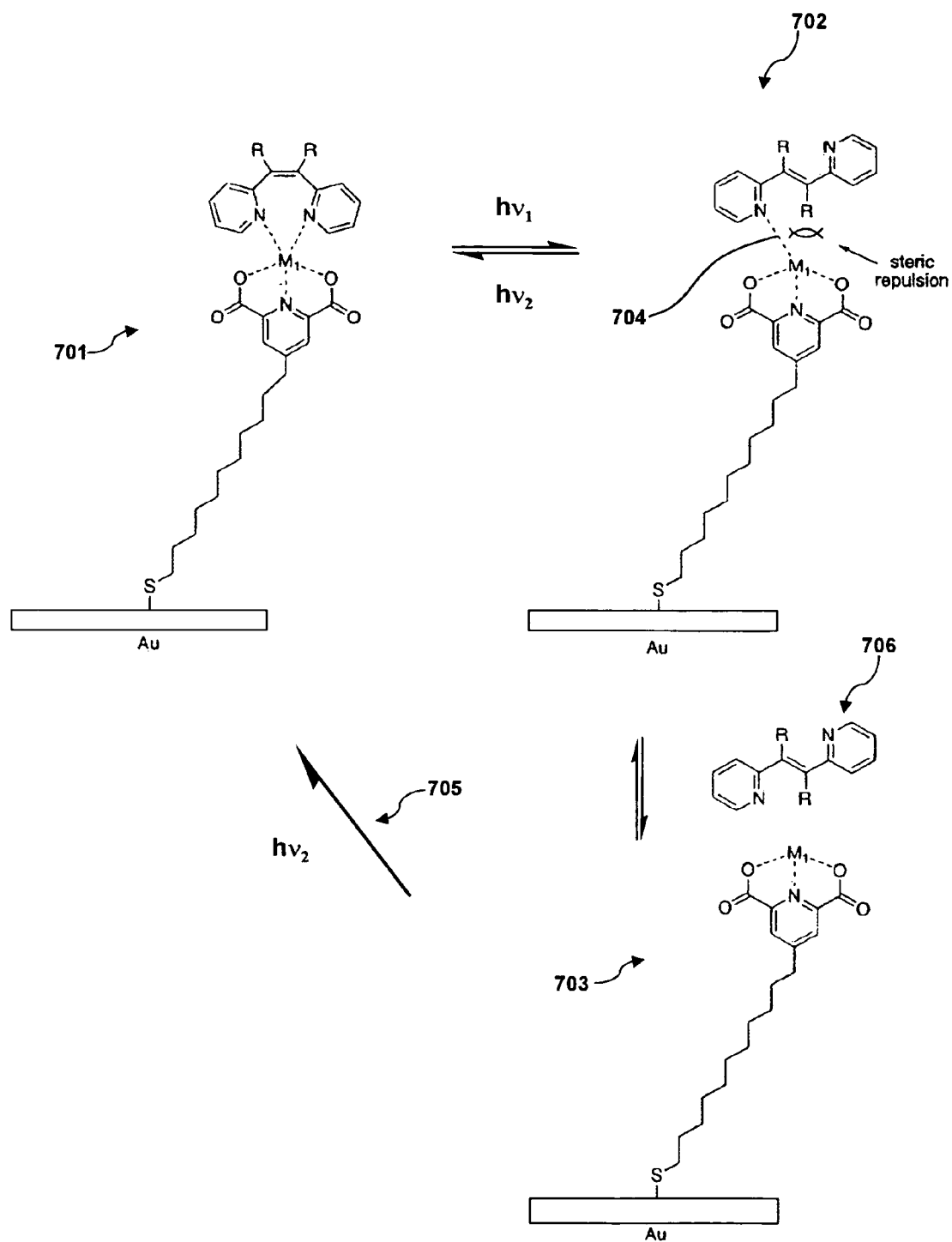
FIG. 7 schematically illustrates various embodiments of a substantially monolayer thick photochromic film with a 2,2'-dipyridylethylene as the photochromic molecule, where the photoresponsive wettability is substantially reversible.

Substantially reversible photoresponsive wettability can be achieved through photoinduced interconversion of a substituted cis-2'2'-dipyridylethylene to the corresponding trans-2,2'-dipyridylethylene where the trans-2,2'-dipyridylethylene units detach from the surface. Detachment of the trans-2,2'-dipyridylethylene units can be achieved, for example, by enhancing the steric repulsion between the trans-2,2'-dipyridylethylene units and the underlying surface. For example, referring to FIG. 7, in various embodiments, substituents R are placed on cis-2,2'-dipyridylethylene at the positions indicated. Preferably, R is a large bulky alkyl, aryl or halogen that introduces steric repulsion and interrupts binding of the 2,2'-dipyridylethylene to the metal ion (Cu(II) when in the trans configuration, but which does not prevent binding of 2'2'-dipyridylethylene in the cis configuration. Prior to irradiation 701, the R groups are oriented away from the metal atom binding site and do not substantially interfere sterically with the binding of the cis-2,2'-dipyridylethylene configuration to the metal atom. Photoinduced conversion of the cis-2,2'-dipyridylethylene to the trans-2,2'-dipyridylethylene 702 causes an R group bridging ethylene to reorient closer to the metal atom capped surface thereby increasing steric repulsion between the trans-2,2'-dipyridylethylene units and the underlying metal atom capped surface. The trans-2'2'-dipyridylethylene units can detach 703 from the metal atom when the steric repulsion from R becomes large enough to break the nitrogen-metal bond 704. The resulting exposure of the underlying metal ions results in a more hydrophilic surface with greater wettability.

Photoinduced conversion 705 of the trans-2,2'-dipyridylethylene units back to the cis-2,2'-dipyridylethylene configuration reduces steric repulsion and promotes reattachment of free cis-2,2'-dipyridylethylene units 706 to the metal atoms.

Monolayers with Substantially Irreversible Photoresponsive Wettability

In various other embodiments, the present invention provides molecular films where the photoconversion is substantially irreversible by irradiation with light. Substantially monolayer thick molecular films with substantially irreversible photoresponsive wettability can be achieved in several ways. In various embodiments, substantially irreversible photoresponsive wettability can be achieved where, although photoconverted configuration remains attached to the metal atom, solvation of the metal atom substantially prevents reversion to the original configuration. Substantially irreversible photoresponsive wettability can also be achieved where the photoconverted configuration detaches from the surface and e.g., forms a complex with a species in solution with a binding energy greater than that between the metal atom and either of the photochromic system configurations.

2,2 2'-DIPYRIDYLETHYLENE EXAMPLE

In various embodiments, a substantially monolayer thick film with a substantially irreversible photoresponsive wettability can be prepared of the general formula $$R_1\text{-}M\text{-}R_2R_3R_4 \quad (VII),$$

where the head group $R_2$ is a dicarboxypyridine, $R_3$ is a $C_{11}$-$C_{16}$ alkyl group, and $R_4$ is chosen based on the substrate to which the film is to be attached, e.g., a thiol group when the substrate is a gold surface. The metal ion is Cu(II) and the photochromic molecule $R_1$ is cis-2,2'-dipyridylethylene which can be deposited from an appropriate solvent (such as ethanol) onto the metal ions, for example, such that once deposited one or more nitrogen and/or oxygen atoms complex with the Cu(II) ion. One of many embodiments of such a film is illustrated in FIG. 5A.

Figure 8A:
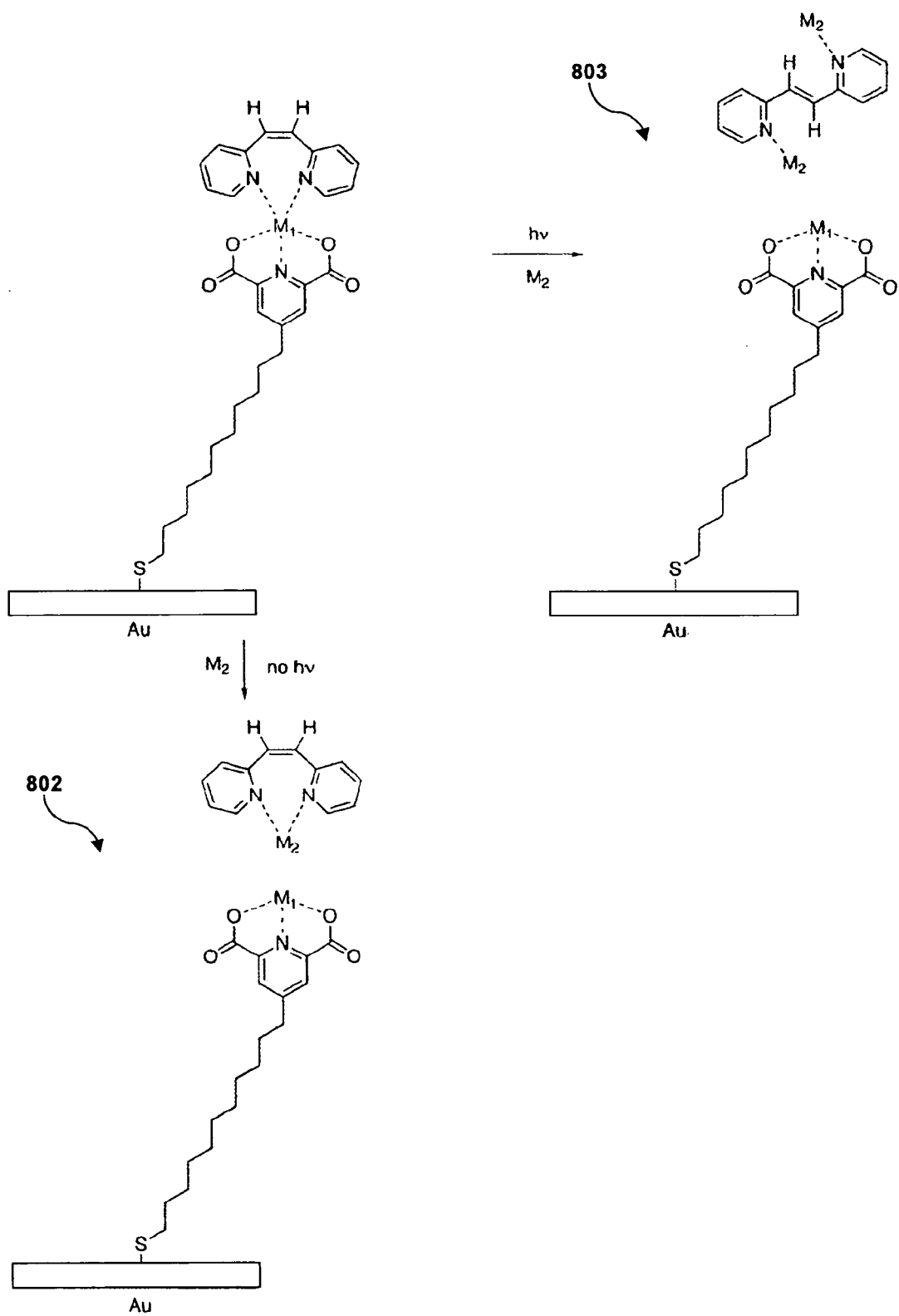
FIGS. 8A and 8B schematically illustrate various embodiments of a substantially monolayer thick photochromic film with a 2,2'-dipyridylethylene as the photochromic molecule, where the photoresponsive wettability is substantially irreversible.

Referring to FIG. 8A, in various embodiments, irreversible detachment of 2,2'-dipyridylethylene units can be achieved by conducting the photoconversion of the cis-2,2'-dipyridylethylene configuration to the trans-2,2'-dipyridylethylene configuration in the presence of an excess of a second metal ($M_2$) that has a higher oxidation state than the metal atom ($M_1$) of the film (e.g., an oxidation state of III or higher where the metal atom in the film has an oxidation state of II). The greater attraction of the dipyridylethylene for $M_2$ leads to competition for binding between $M_1$ and $M_2$ that can result in the direct detachment 802 of the cis-2,2'-dipyridylethylene configuration prior to irradiation, the irreversible detachment of the trans-2,2'-dipyridylethylene after photoconversion 803, or both.

Figure 8B:
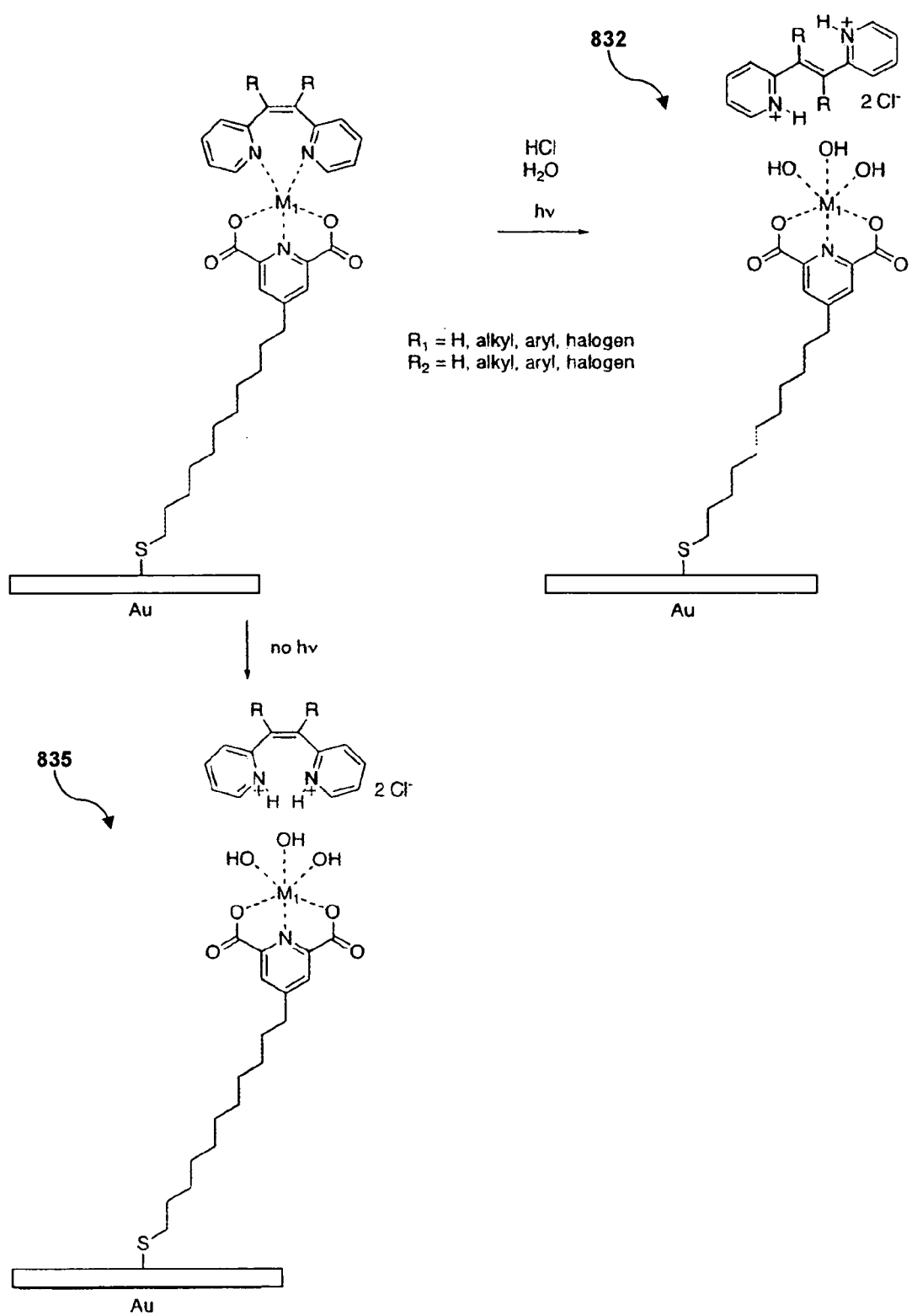

Referring to FIG. 8B, in various embodiments, irreversible detachment of 2,2'-dipyridylethylene groups can be achieved, for example, by conducting the photoconversion of the cis-2,2'-dipyridylethylene configuration to the trans-2,2'-dipyridylethylene configuration in the presence of aqueous acid. Conversion of cis-2,2'-dipyridylethylene can result in trans-2,2'-dipyridylethylene units bound to the metal atom by a single bond. Protonation of the pyridine nitrogen atoms by acid to form pyridinium ions can subsequently promote detachment 832 of the trans-2,2'-dipyridylethylene units from the metal atom. The protonation of the pyridine nitrogen atoms by acid to form pyridinium ions can also result in the direct detachment 835 of the cis-2,2'-dipyridylethylene configuration prior to irradiation.

In principle, this method of detachment can be reversed (i.e., substantially reversible wettability provided) if a suitable base is introduced to deprotonate the pyridinium groups and regenerate neutral trans-2,2'-dipyridylethylene in solution, followed by photoinduced conversion of the trans-2'2'-dipyridylethylene units to cis-2,2'-dipyridylethylene units which can reattach to the metal atoms.

Photochromic Articles

In various aspects, the present invention provides photochromic articles comprising a substrate having a surface with substantially monolayer thick molecular film that has a photoresponsive wettability covering at least a portion of the surface. The molecular film comprises molecules of the general formula (I): $R_1$—M—$R_2(X)_m R_3 R_4$, which are attached to a surface of the substrate substantially via $R_4$.

In various embodiments, the photochromic article comprises one or more regions having substantially reversible photoresponsive wettability that are configured for fluid manipulation.

In various embodiments, the photochromic article comprises one or more regions having photoresponsive wettability that are configured for one or more of metal centered redox chemistry or heterogeneous catalysis.

In various embodiments, the photochromic article comprises one or more regions having substantially reversible photoresponsive wettability that are configured for molecular separation. Entropic recoil separation is a biopolymer separation method based on an entropic force caused by spatial confinement of molecules. For example, when a polymer lies across an interface between a high-entropy and a low-entropy region, it will spontaneously retract from the low-entropy region. In various embodiments, the present invention provides a photochromic article having a surface with a substantially reversible photoresponsive wettability, comprising a series of nanoscale lines (lines with a width on the order of 100 nm wide or smaller) of hydrophobic surface interspersed between nanoscale lines of hydrophillic surface. The hydrophobic and/or hydrophilic lines can be static, or dynamic (e.g., hydophibicity and/or hydrophobicity is switched on or off by irradiations with light). In various embodiments, the nanoscale lines can be ordered such that diffraction lines can be used to pattern the surface with the nanoscale lines.

Formation of Micro- and Nanofluidic Structures

In various embodiments, the films of the present invention can be used to facilitate fabrication or to fabricate micro- and nanofluidic structures and devices. Such structures can be fabricated with various embodiments of detachable, molecular films and non-detachable or both, of the present inventions. For example, in various embodiments, by selectively photoexciting the photochromic material on a surface (e.g., using a a lamp passing through a 'mask' with a desired pattern or by using a laser, the output of which can be moved across the surface in a controlled fashion,) highly complex 2-dimensional patterns can be created in which the regions exposed to light will have a different wettabilty than regions that were unexposed. While it is believed, without being held to theory, that significant changes in wettability can be achieved for photochromic systems that are non-detachable, it is preferred and believed, without being held to theory, that greater differentiation in the wettability between photoexcited and non-photoexcited regions can be achieved in detachable photochromic systems in which the underlying metal ion is exposed. These exposed surfaces, for example, can provide the opportunity to create micro/nanofluidic devices in which the fluidic channels are created not by lithography of an underlying substrate to create three dimensional structures on the microscale, but by creating essentially two-dimensional channels (or lanes) of high wettability. In the case of detachable surfaces, there is a very small degree of three dimensionality (on the nm scale) do to the detachment of at least a portion of the photochromic molecule, i.e., or substantially no three dimensionality to these devices on microscopic scales, because only one of the molecular layers is removed (about a 1 nm change in the thickness of the film). In the case of non-detachable systems, there is substantially no three dimensional change upon photoexcitation. Accordingly a nano/microfluidic channel provided using a molecular film of the present invention can be in effect a virtual one in terms of spatial depth, but nevertheless an obviously a real channel (or lane) in terms of wettability.

In various embodiments, highly wettable nano/micro channels created in this way can allow the transport of fluids (e.g., water and other hydrophilic fluids, hydrophobic fluids, or both depending, e.g., on the gradient in surface free energy) by forces, it is believed, without being held to theory, that are similar to those found in capillary action. In various embodiments, the ability to separately control the flow of hydrophilic and hydrophobic liquids in micro or nanochannels can facilitate creating a high degree of complexity in the nano/microfluidic devices produced.

In various embodiments, highly complex, and therefore potentially more highly functional fluidic devices, can be created using photochromic systems that are detachable. In such systems, e.g., specific regions can be stripped of their light absorbing compounds and other material deposited in their place. These new materials can have absorption in different regions of the spectrum and thereby allow them, e.g., to be resistant to isomerization under the photoexcitation conditions used to detach the original light absorbing molecules from the metal atoms of the molecular film. In various embodiments, photoexcitation at the original wavelength could then be used to create another pattern of exposed metal atoms followed by another deposition of a different material. This process can be repeated so as to create highly complex two-dimensional patterns of wettability. In addition, by depositing a fresh layer of ligands and metal atoms and photochromic molecules, complex 3-dimensional patterns of wettabilty can also be created in various embodiments.

EXAMPLES

The present invention will be more fully described by the following non-limiting examples.

Example 1

Alkyl-pyridine-2,6-dicarboxylic, Cu(II), dipyridylethylene films

A. Results and Discussion:

This example presents various embodiments of assembled substantially monolayer thick molecular films, Films I and II. Films I and II can be schematically illustrated as shown in FIG. 5A. Each film comprises a 2,2'-dipyridylethylene photochromic molecule 508, 514 coupled to a gold surface via a metal atom 502 (Cu (II) which in turn is coupled to a organic tethering molecule 503 (4-[(10-mercaptodecyl)oxy] pyridine-2,6-dicarboxylate) by metal-ligand interactions). Film I 520 being the molecular film with the cis-2,2'-dipyridylethylene photochromic molecule configuration and Film II 522 being the molecular film with the trans-2,2'-dipyridylethylene photochromic molecule configuration.

Films I and II were fabricated by self assembly of 4-[(10-mercaptodecyl)oxy]pyridine-2,6-dicarboxylic acid on a clean gold surface, followed by the deposition of Cu(II) ions (from $CuBr_2$) that complex with the pyridine head group of the organic tethering molecule layer, and finally by deposition of the 2,2'-dipyridylethylene in either the cis form (Film I) or trans form (Film II), which serves to cap the Cu(II) ions. Conductivity, impedance, contact angle and grazing incidence IR experiments were carried out on Films I and II after the addition of each layer. These experiments confirmed the ordered deposition of each component of the molecular film.

Conductivity (CV) values for both Films I and II, obtained in an aqueous solution of $K_3[Fe(CN)_6]$, changed as the individual components were deposited sequentially onto the gold surface. The CV of the bare gold surface shows the $Fe^{3+}/Fe^{2+}$ redox peaks for oxidation and reduction of ferricyanide, whereas deposition of the pyridine-capped decanethiol yielded conductivity values (measured in the range −0.5 V-+0.6 V versus a saturated calomel electrode (SCE) ($Hg/Hg_2Cl_2$, KCl (sat'd)) indicated the formation of an insulating monolayer with few defects. After the monolayer was exposed to a solution of Cu(II) ions, the CV of the film was nearly identical to that of bare gold with only a small decrease in peak current. This result indicated that the Cu(II) ions promote tunneling of electrons between the gold surface and the solution. Deposition of the dipyridylethylene ligands resulted in attenuated conductivity consistent with the formation of an insulating layer on the surface.

Contact angle measurements of Film I (cis-2,2'dipyrydylehtylene photochromic molecule), both as formed and irradiated, and Film II (trans-2,2'dipyrydylehtylene photochromic molecule), both as formed and irradiated, are given in Table 1. In addition, Table 1 provides the contact angle measursments for the gold surface, the gold surface functionalized with a substantially monolayer thick self assembled film of 4-[(10-mercaptodecyl)oxy]pyridine-2,6-dicarboxylate, and a substantially monolayer thick film of 4-[(10 mercaptodecyl)oxy]pyridine-2,6-dicarboxylate with the pyridine head groups complexed with Cu(II).

Table 1 illustrates a substantial change in contact angle (about 20.5°) after irradiation with 300 nm light photoconverting the cis-2,2'dipyridylethylene surface of the film to trans-2,2'dipyrydylehtylene. FIG. 5A schematically illustrates the photoconversion of a cis form of the photochromic molecule 5082 in Film I 520 to a trans form of the photochromic molecule 514 in Film II 522.

TABLE I

| Film/Surface | Contact Angle (degrees) |
| --- | --- |
| Gold | 76 ± 1.0 |
| Film I | |
| Component 1 (pyridyl-capped decanethiol) | 76.0 ± 1.5 |
| Component 2 (Cu(II) ions) | 58.0 ± 2.0 |
| Component 3 (cis-2,2'dipyrydylehtylene) | 76.5 ± 2.5 |
| Film II | |
| Component 3 (trans-2,2'dipyrydylehtylene) | 63.5 ± 0.5 |
| Film I Irradiated | 57.0 ± 2.0 |
| Film II Irradiated | 64.0 ± 2.0 |

Table 1 illustrates that deposition of cis and trans-dipyridylethylene leads to differences in the surface wettability with the cis-isomer providing a more hydrophobic surface as determined from contact angle measurements. The difference in contact angle of about 13° between Film I and II is greater than that reported for a variety of photoisomerizable thin films that typically exhibit changes of around 9°.

Figure 9:
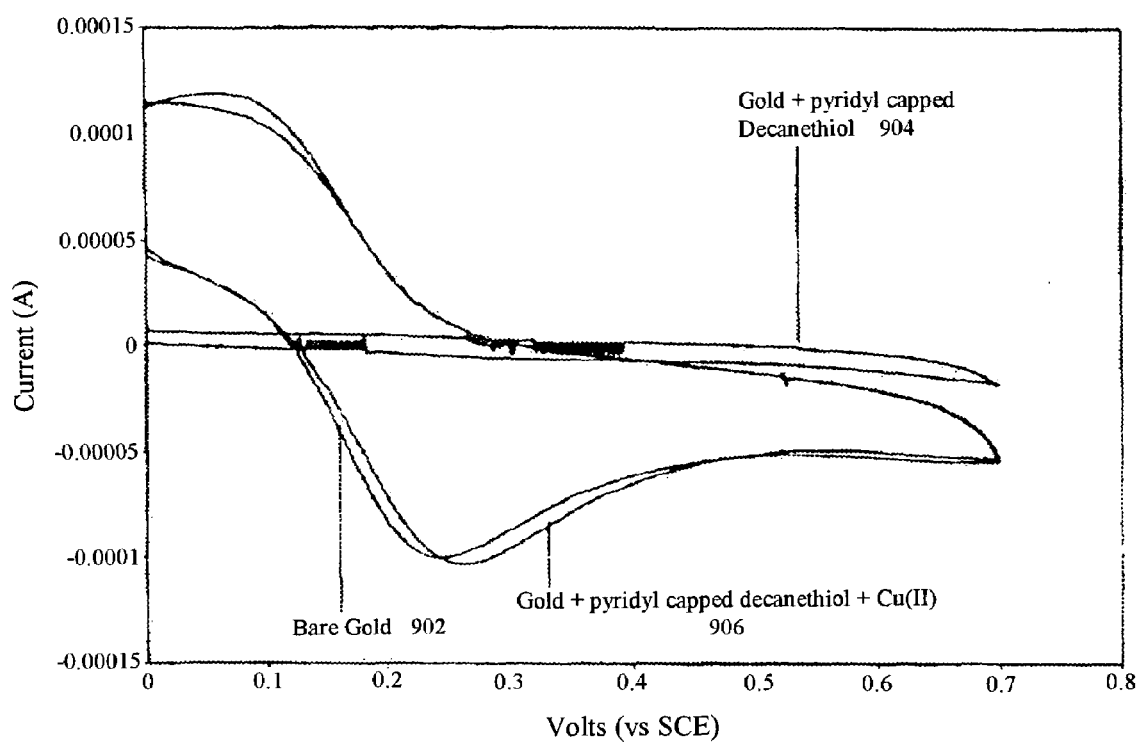
FIGS. 9 and 10 depict experimental data of Example 1, comparing cyclic voltammagrams of various films in this example.
Figure 10:
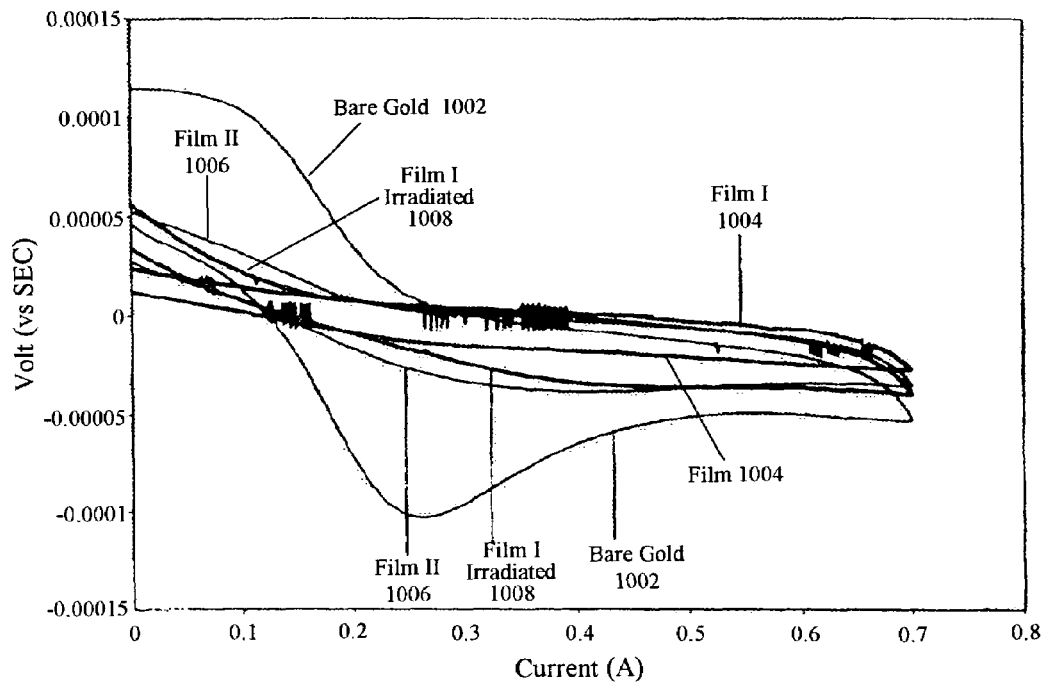

The CV results indicate that the cis-capped surface is less conductive than the trans-capped surface. FIGS. 9 and 10 depict experimental data comparing cyclic voltammagrams of various films and components, and Table 2 summarizes the results of the impedance measurements. Referring to FIGS. 9 and 10, cyclic voltammograms are shown for a bare gold surface 902, 1002, a surface covered with a substantially monolayer thick 4-[(10 mercaptodecyl)oxy]pyridine-2,6-dicarboxylate surface 904, a surface covered with a substantially monolayer thick surface of Cu(II) capped 4-[(10 mercaptodecyl)oxy]pyridine-2,6-dicarboxylate 906, a substantially monolayer thick Film I surface 1004, a substantially monolayer thick Film II surface 1006, and a substantially monolayer thick Film I surface after irradiation 1008.

Recalling that impedance measurements indicate well ordered films in each case and that the IR experimental results confirm the presence of the dipyridylethylene in each film, the difference in surface hydrophobicity can be attributed to differences in the electrostatics of the two surfaces that arise from different orientations of the two isomers.

TABLE 2

| Sample | $R_{sol}$ (ohms) | $R_{SAM}$ (ohms) | $C_{dl}$ (µF) |
| --- | --- | --- | --- |
| Pyridine decanethiol | 148.6 | 12995.0 | 8.44 |
| Pyridine decanethiol/Cu | 79.7 | 6551.3 | 16.96 |
| Film I | 154.1 | 11076.0 | 10.13 |
| Film II | 155.4 | 8742.7 | 13.70 |
| Film I (irradiated) | 135.9 | 7825.3 | 14.48 |

Molecular modeling and previous studies of nickeldipyridylethylene complexes indicate that the cis-isomer can form a symmetrical bidentate Cu(II) complex that efficiently 'caps' the metal ion; which is consistent with a hydrophobic packing arrangement on the surface of Film I. The trans-isomer, however, typically is not able to form a stable bidentate complex; instead, the binding of the trans-isomer is likely monodentate. The schematic structures illustrated in FIG. 5A facilitate understanding the enhanced wettability provided by the trans isomer because the Cu(II) ion, in this example, is not completely coordinated and, therefore, is free to complex with water. Impedance measurements on Film II in fact show elevated capacitance values for the trans-capped system, which indicates that diffusion occurs between the solution and the layer of metal ions.

The contact angle, CV, impedance and IR data also facilitate understanding the changes that occur following photoexcitation of the films of this example. Exposure of Film I to 300 nm irradiation in chloroform, in the presence or the absence of oxygen, results in a substantial decrease in the contact angle, from 76.5° to 57°. The contact angle obtained is somewhat smaller than that of unirradiated Film 11 and is believed, without being held to theory, to be the result of different packing arrangements in the molecular films. Also, the conductivity of Film I increases following irradiation so as to be nearly identical to that of the unirradiated Film II, while impedance measurements indicate that the irradiated film remains a well ordered system. The clearest confirmation of isomerization of Film I is provided by the IR reflectance measurements.

FIGS. 11-18 shows IR reflectance spectra comparing various films and components of this example at various wavelengths. Referring to FIGS. 11-17, IR reflectance spectra are shown for a substantially monolayer thick Film I surface 1102, 1202, 1302, 1402, 1502, a substantially monolayer thick Film II surface 1104, 1204, 1304, 1404, 1504, 1604, 1704 a substantially monolayer thick Film I surface after irradiation 1106, 1406, 1506 a substantially monolayer thick Film II surface after irradiation 1608, 1708.

Figure 11:
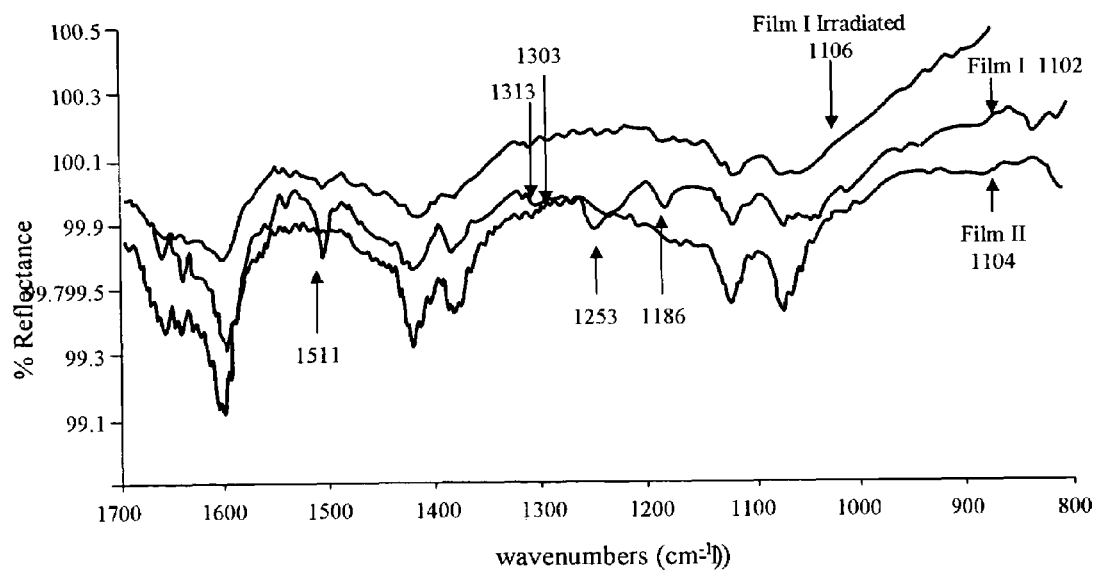
FIGS. 11-18 depict experimental data of Example 1, comparing IR reflectance spectra of various films in this example over various wavelength ranges and under various conditions.
Figure 12:
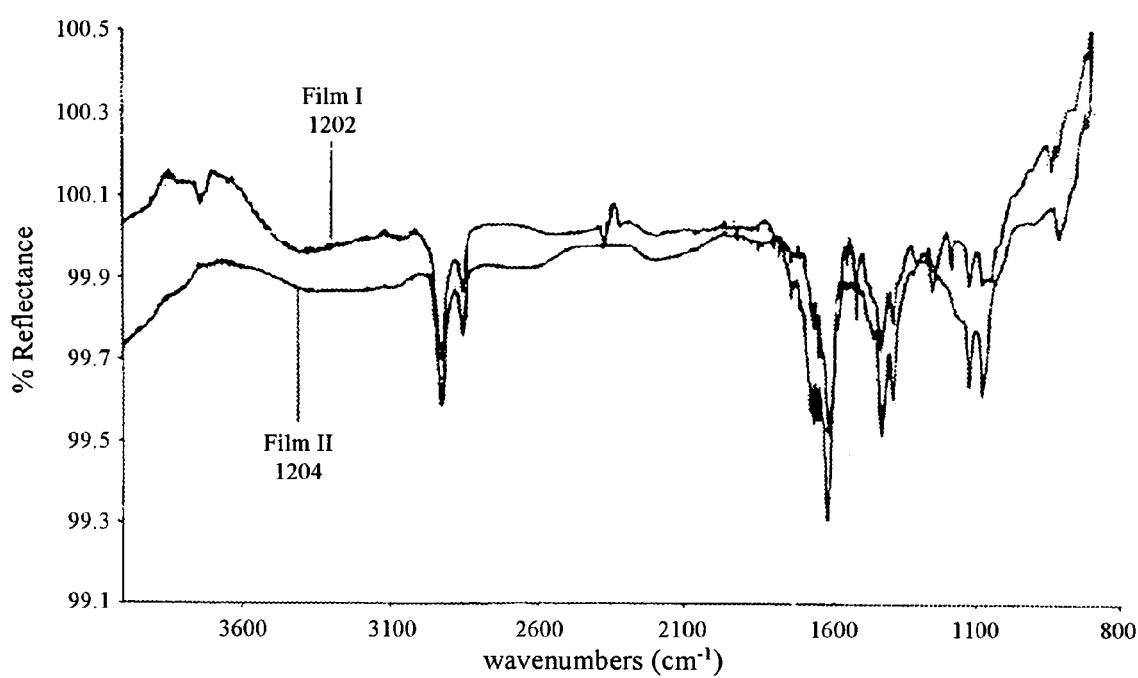
Figure 13:
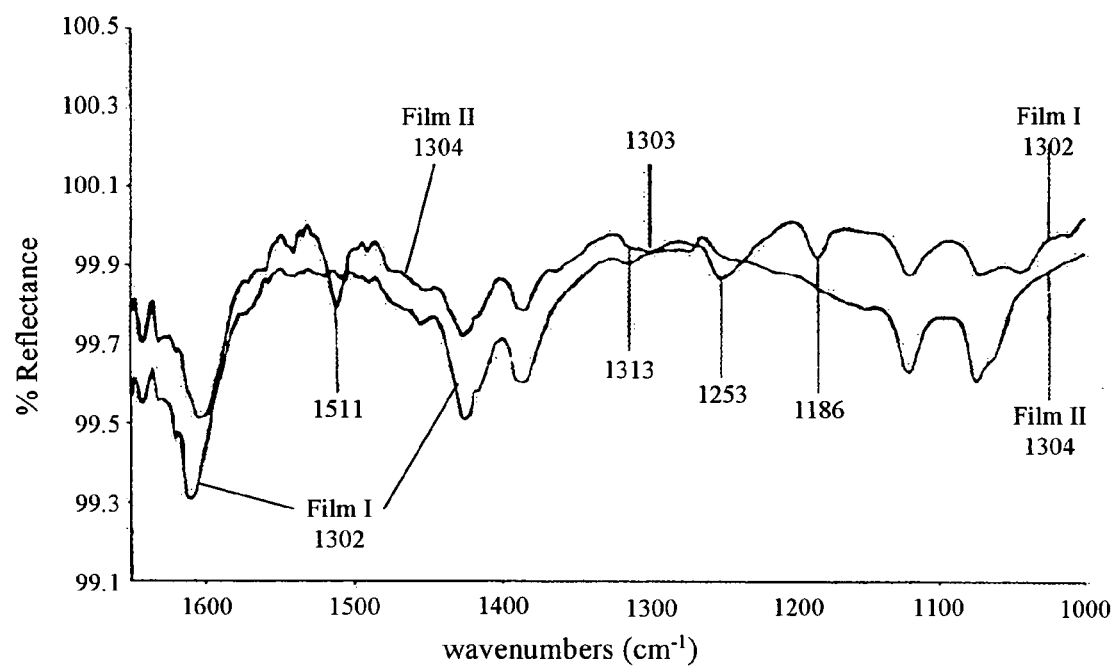
Figure 14:
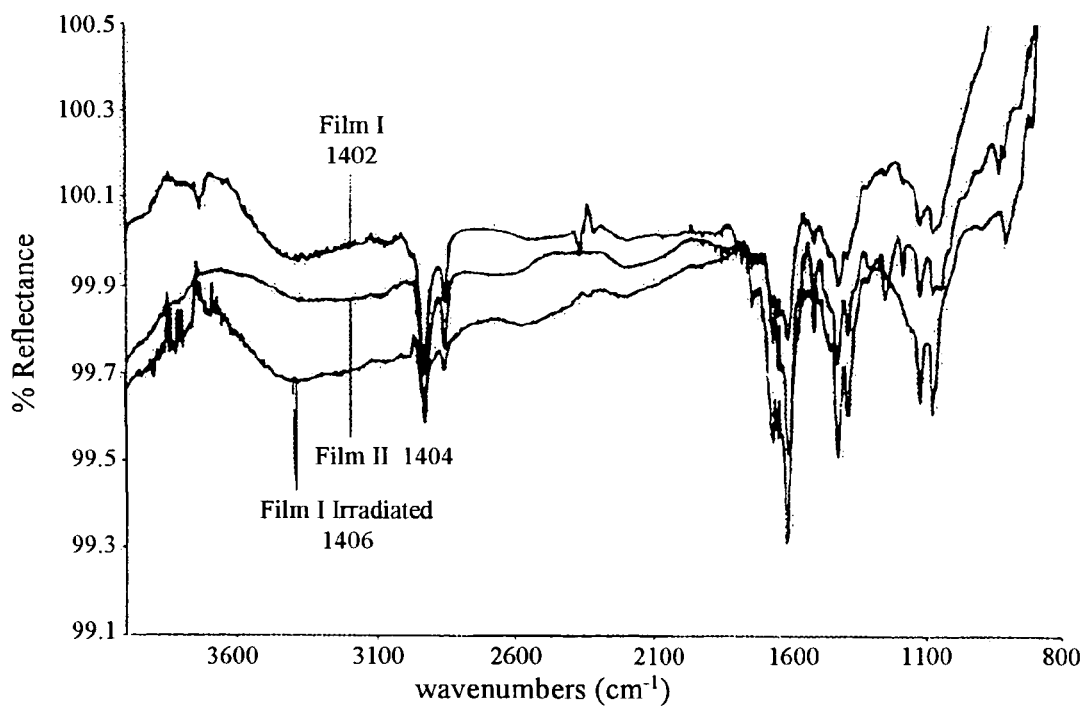
Figure 15:
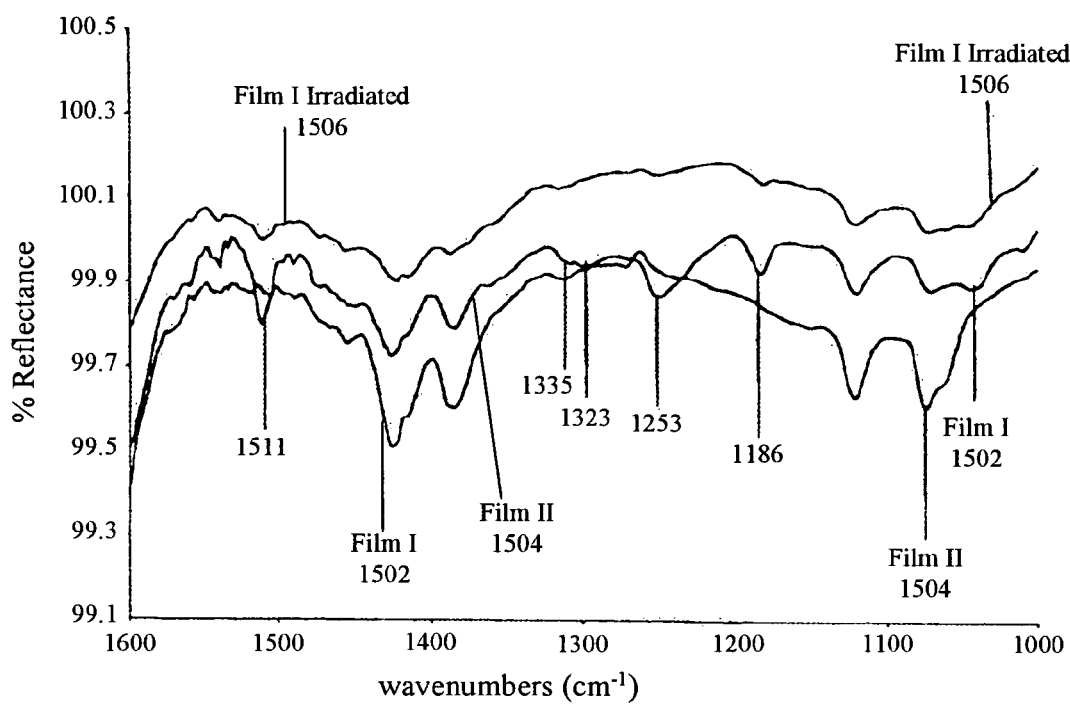
Figure 16:
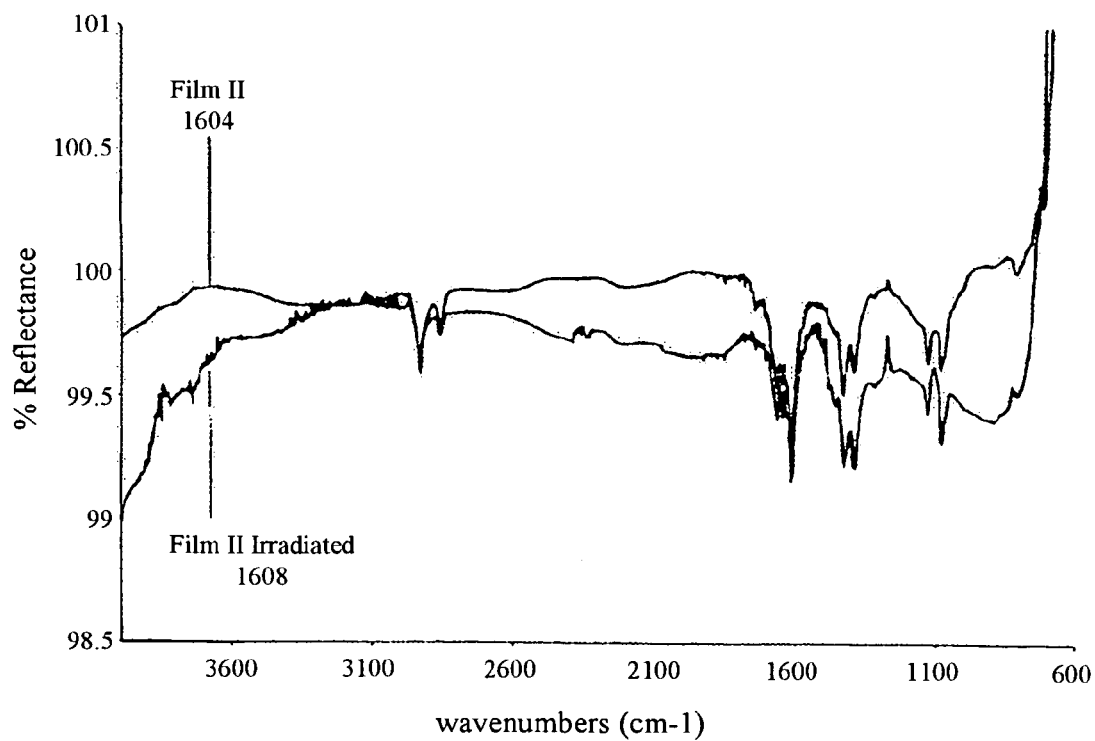
Figure 17:
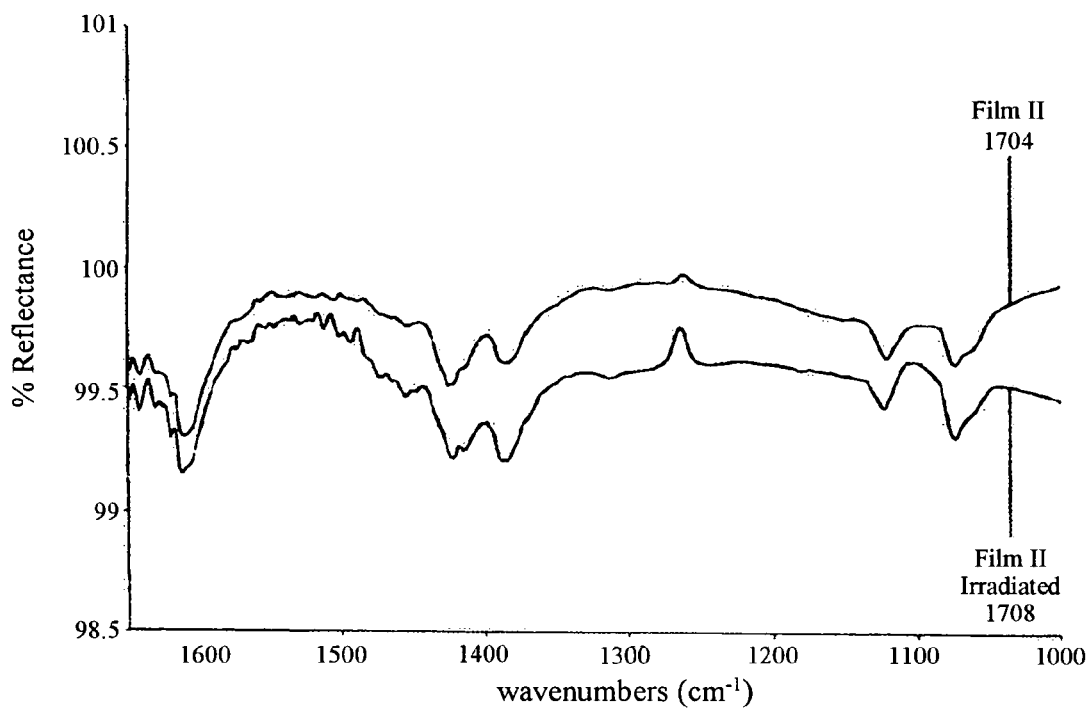

FIG. 11 depicts the spectra of the unirradiated Films I and II and Film I following irradiation. While the IR absorption bands that are normally used to distinguish between cis- and trans-dipyridylethylenes lie at frequencies lower than 1000 cm$^{-1}$, the sensitivity of the grazing incidence IR instrument used in this example is low in this region. There are several aromatic stretching frequencies that absorb above 1000 cm$^{-1}$, however, that are found in the spectrum of unirradiated Film I but are absent in the spectrum of Film II. For example, Film I absorbs strongly at 1511 cm$^{-1}$ and less intensely at 1313, 1303, 1253, and 1186 cm$^{-1}$, while Film II does not. Following irradiation of Film I, these bands are attenuated and the spectrum of irradiated Film I closely resembles that of Film II. Previous studies on the solution photochemistry of 2,2'-dipyridylethylenes report quantum yields for cis-trans and transcis photoisomerization equal to 0.84 and 0.12, respectively. Irradiation of Film II, however, does not yield substantially any cis product as indicated by the lack of change in the CV, IR and contact angle data for irradiated Film II. It is believed, without being held to theory, that the failure of the trans-dipyridylethylene units to undergo photoisomerization to the cis isomers is due at least in part to an ordered packing of the trans-dipyridylethylene units in Film II that sterically inhibits the structural reorganization necessary for trans-cis isomerization to occur. The CV and impedance measurements of Film II indicate that the dipyridylethylene head groups are well ordered in Film II.

Further details regarding the materials, analytical instruments and measurements of Example 1 follow.

B. Materials:

Most reagents and solvents used in the synthesis of the components of Films I and II in this example were purchased from Aldrich and were used without further purification. Chelidamic acid was purchased from Fluka.

C. Analytic Instruments:

NMR spectra were obtained with an Avance Bruker NMR spectrometer at 400 MHz for proton and 85 MHz for $^{13}$C. All NMR spectra were obtained in deuterochloroform solutions, unless otherwise noted. Mass spectra were obtained from the SynPep Corporation. Ionization was performed using electrospray, with acetonitrile as the carrier solvent, and nitrogen as a curtain gas.

C. Synthesis of the Molecular Components Contained in Films I and II.

1. Synthesis of 4-[(10-mercaptodecyl)oxy]pyridine-2,6-dicarboxylic acid (i) Diethyl 4-hydroxypyridine-2,6-dicarboxylate 6.2 mL of thionyl chloride (85 mmol) was slowly added to 25 mL of absolute ethanol at 0° C. To this solution 2.5 g (13.7 mmol) of chelidamic acid was added. The solution was stirred at room temperature for 18 h, and refluxed for 2 h to ensure completeness. Solvent was removed under reduced pressure, and 20 mL of distilled water was added to the crude product at 0° C. The mixture was neutralized with 5 mL of 10% aqueous sodium carbonate and 5 mL of 50% aqueous ethanol. The white precipitate was filtered and dried under vacuum to afford 3.26 g of product. Yield: 99%, R$_f$=0.65 (MeOH), m.p.: 115-116°; $^1$H-NMR δ(ppm) 1.45 (t, 6H, CH$_3$); 4.46 (q, 4H, CH$_2$); 7.31 (m, 2H, aromatic); 9.96 (bs, 1H, OH); $^{13}$C NMR δ(ppm) 14.5 (CH$_3$); 63.9 (CH$_2$); 120.8 (Ar-C); EST-MS: (M+Na)$^+$ 262.3 (calc. 262.2)

(ii) Diethyl 4-[(10-Bromodecyl)oxy]pyridine-2,6-dicarboxylate 2 g (8.4 mmol) of diethyl 4-hydroxypyridine,-2,6-dicarboxylate and 7.6 g (25.2 mmol) of 1,10 dibromodecane were dissolved in 100 mL of dryacetone. 2.32 g (16.8 mmol) of potassium carbonate was added. The solution was heated to reflux for 40 h. The reaction was followed by normal phase TLC (1:1 chloroform:hexane). The solvent was removed under reduced pressure, and the residue dissolved in a minimal amount of dichloromethane. The solution was filtered, and the solvent was again evaporated. The resultant residue was purified on silica gel with 1:1 dichlormethane:hexane as the eluent to yield 2.89 g of product. Yield 75%; $^1$H-NMR δ(ppm) 1.24-1.28 (m, 20 H, 14 from decyl CH$_2$, 6 from CH$_3$); 1.86 (m, 2H, CH$_2$CH$_2$Br); 3.41 (t, 2H, CH$_2$Br); 4.13 (t, 2H, O CH$_2$(CH$_2$)$_9$Br); 4.48 (q, 4H, O—CH$_2$CH$_3$); 7.74 (s, 2H, aromatic); $^{13}$C-NMR δ(ppm) 14.6 (CH$_3$); 26.2, 28.5, 29.1, 29.6, 29.7, 29.8, 33.2, 34.5 (CH$_2$); 60.8, 69.4 (O CH$_2$); 114.7, 150.5, 165.2 (aromatic C); 167.4 (C=O).

(iii) Diethyl 4-[(lo-Thioacetyldecyl)oxy]pyridine-2,6-dicarboxylate 1.20 g (2.6 mmol) of diethyl 4-(10-bromodecyloxy)-pyridine-2,3-dicarboxylate and 0.35 g (3.36 mmol) of potassium thioacetate were dissolved in 100 mL of ethanol and the solution brought to reflux for 24 h. The resulting white precipitate was filtered and dried under vacuum. The product was used in subsequent steps without further purification or characterization due to its low solubility in most organic solvents.

(iv) 4-[(10-mercaptodecyl)oxy]pyridine-2,6-dicarboxylic acid 1.13 g of the product obtained in the previous step was suspended in 75 mL of 2 N KOH solution (in 70% aqueous ethanol). The solution was stirred for 15 minutes and the reaction quenched by acidifiying with glacial acetic acid. The solvent was removed under reduced pressure, and the crude residue dissolved in dichloromethane. The organic fraction was washed with 1 N NaOH, and the organic phase discarded. The aqueous phase was acidified with 3 N HCl, and extracted with 3 25 mL portions of dichloromethane. The organic fractions were combined, and the solvent removed under reduced pressure to yield a white powder. $^1$H-NMR δ(ppm) 1.24-1.44 (m, 16H, decyl CH$_2$); 1.85 (bs, 1H, SH); 2.5 1 (m, 2H, CH$_2$SH); 4.23 (m, 2H, O—CH$_2$); 6.49 (bs, 2H, COOH); 7.88 (s, 2H, aromatic); ESI-MS (M+H)$^+$ 356.2 (calc 356.4).

2. Synthesis of Cis-(2,2'-dipyridyl)ethylene 2 g (10.9 mmol) of trans-(2,2'-dipyridyl)ethylene was dissolved in 75 mL of spectroscopic grade chloroform, and placed in a large pyrex tube. The tube was placed in a rotary photoreactor, and irradiated at 300 nm for a period of 1 h. The chloroform was removed under reduced pressure, and the crude product purified over silica gel using 15:1 chloroform:methanol as the mobile phase to yield 0.3 g of the yellow cis product. Yield: 15%, R$_f$0.4 (15:1 CHCl$_3$:MeOH), GCMS r.t.=12 min at 200° C., [M]$^+$ 155; $^1$H-NMR δ(ppm)

6.81 (s, 2H, ethylene CH$_2$); 7.05 (m, 1H, NCHCHCH in ring); 7.20 (d, 1H, NCCHCH in ring); 7.42 (m, 1H, NCHCHCH in ring); 8.56 (d, 1H, NCHCH in ring); $^{13}$C NMR δ(ppm) 122.4 (ethylene CH); 124.2, 133.3, 136.4, 149.8, 155.9 (aromatic CH groups).

Preparation of Self Assembled Monolayers

Gold slides were purchased from Evaporated Meatal Films (EMF). The slides have dimensions of 25 mm×75 mm×1 mm of float glass with cut edges, and are coated with 50 angstroms (Å) of Cr followed by 1000 Å of Au. The substrates were cut into different sizes according to experimental needs. Prior to use, the substrates were immersed in piranha solution (70% sulfuric acid, 30% hydrogen peroxide (30% aqueous)) at 90° C. for 20 minutes to clean the surface. The slides were then washed with deionized water, dried with nitrogen, and used immediately. Monolayers were prepared by immersing the clean gold slides in a 1-2 mM ethanol solution of the desired compound. For 4-[(10-mercaptodecyl)oxy]pyridine-2,6-dicarboxylic acid solutions, full coverage of the surfaces was reached after 6 h, as evidenced by no further changes in the contact angle measurements. Copper (II) bromide was used as the source of Cu(II) ions (1 mM). Full complexation was reached after 3 h of submersion. Capping of the copper ions with the cis and trans dipyridyl ethylenes was done with 5 mM solutions dissolved in either ethanol or acetone. Coverage was completed after 8 h of exposure. After each deposition, the films were rinsed with ethanol, and dried under nitrogen.

Cyclic Voltammetry

All electrochemistry experiments were carried out with an EG&G Princeton Applied Research Potentiostat/Galvanostat Model 273. A three-electrode setup was used with the substrate (at various stages of coating) as the working electrode, a SCE as the reference electrode, and platinum wire as the counter electrode. The monolayer was contacted with an alligator clap, and an area of 1 cm$^2$ was always kept immersed in solution. All solutions were freshly prepared and degassed with nitrogen before the experiments. The aqueous solution used for the experiments was 2 mM potassium ferrocyanide with 50 mM potassium chloride as a supporting electrolyte. To limit noise, the electrochemical cell was placed inside a Faraday cage. The cyclic voltammetry curves were obtained in the range of 0.0 to 0.7 V, with a scan rate of 50 mV/s and a scan increment of 1 V.

Contact Angle Measurements

Contact angle measurements were obtained with a Rame-Hart Model 100-00 Goniometer. 10 pL droplets of water were added to each surface using a calibrated Epindorf pipette.

Infrared Spectroscopy

IR spectra were obtained on a Nexus FT-IR spectrometer equipped with a ThermoNicolet grazing angle accessory and a liquid-nitrogen cooled MCTA detector. The IR beam was incident at 75δ on the gold substrates. The optical path was purged with nitrogen gas before and during data acquisition. Backgrounds were collected before every sample run. For each sample, 64 scans were collected with a 4 cm$^{-1}$ resolution. The scan range was form 4000 to 600 cm$^{-1}$, although the detector cutoff occured at just under 1000 cm$^{-1}$.

The IR spectra, and absorbance assignments for the individual constituents in Films I and II have been described previously. The IR spectra presented focus on the spectra of Films I, II, and irradiated Film I. Examples of bands of interest for comparing these systems occur at 1511, 1313, 1303, 1253, and 1186 cm$^{-1}$ (wavenumbers).

Impedance Spectroscopy

Impedance experiments were performed using a three-electrode setup with the coated substrate as the working electrode (W.E.), a SCE as the reference electrode, and platinum wire as the counter electrode (C.E.). The electrolyte used was a 0.1 M solution of Na2S04 in deionized water. A 1255-HF frequency response analyzer was used in combination with a EG&G Princeton Applied Research Potentiostat/Galvanostat Model 273. The experiment was carried out collecting 20 points per decade, at a fixed potential of −0.5 V, with an amplitude of 20 mV, over a frequency range of 100,000 to 0.01 Hz. The working electrode area was kept at 1 cm$^2$ for all experiments.

Figure 19:
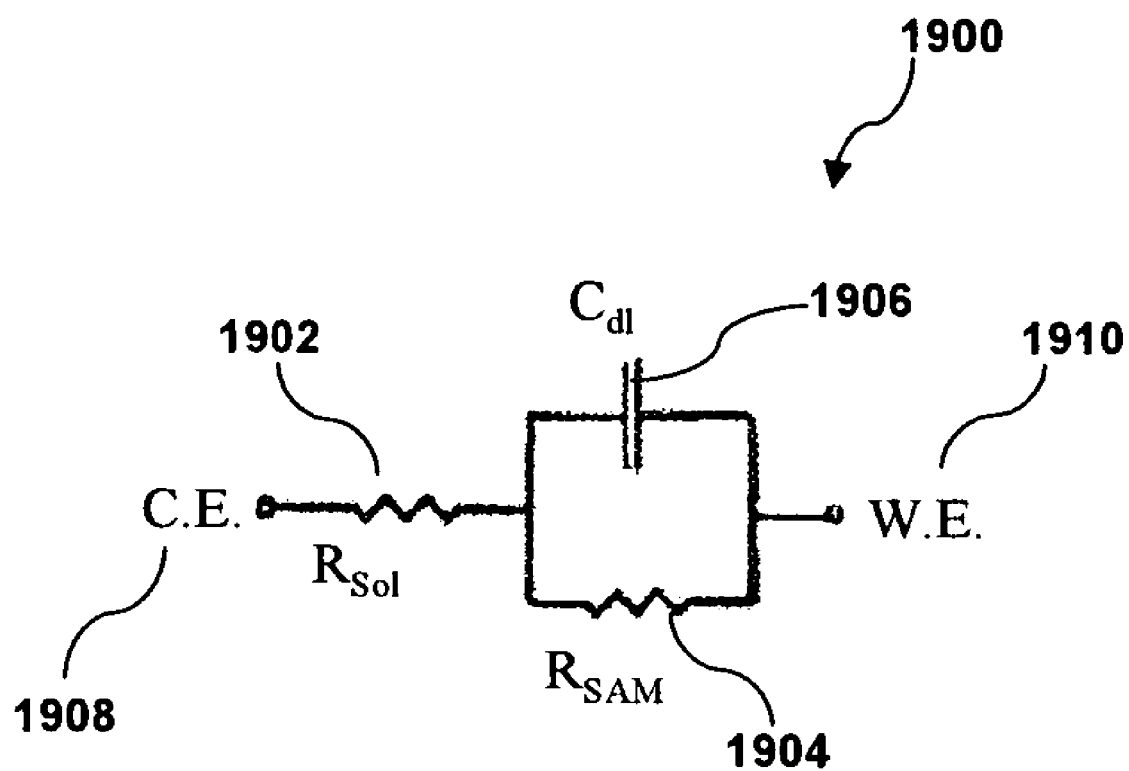
FIG. 19 depicts a Randles equivalence circuit for the impedance measurements of Example 1.

The impedance measurements were represented with both Nyquist and Bode plots. Referring to FIG. 19, a simple Randles equivalent circuit 1900 ($R_{sol}$ 1902 in series with a parallel combination of $R_{SAM}$ 1904 and $C_{dl}$ 1906 as shown in FIG. 19 was used), where $R_{sol}$ 1902 represents the resistance of the solution, $R_{SAM}$ 1904 the resistance of the coated substrate, $C_{dl}$ 1908, W.E. represents the working electrode 1910, and C.E. represents the counter electrode 1912. $R_{sol}$ and $R_{SAM}$ values were obtained from both plots and averaged. $C_{dl}$ was obtained by using equation 1 ($\theta_{max}$, was obtained from the Bode phase plot). Table 2 shows the main results for the different monolayer components applying the analogous circuit from FIG. 19.

$$\omega^{\theta max}=(1/C_{dl}R_{SAM})(1+R_{SAM}/R_{sol})^{1/2} \quad (1),$$

where $\omega^{\theta max}=2\pi v^{\theta max}$.

Photo-Induced Isomerization of Films.

Figure 18:
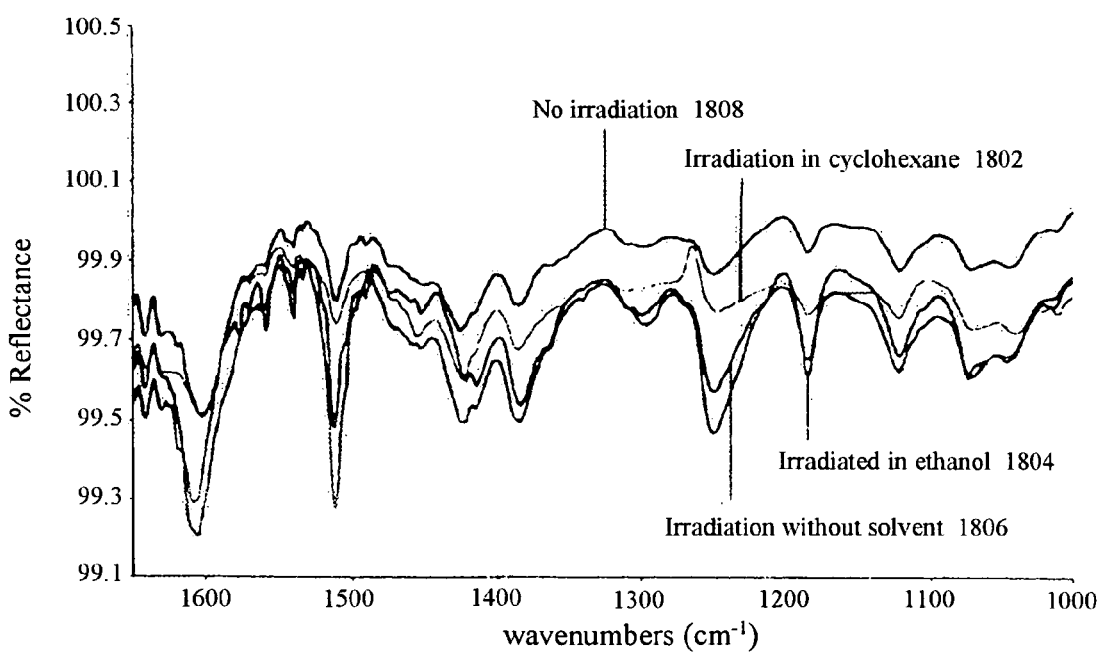

The isomerization of dipyridyl ethylene capped films was attemped by submersing the substrate in chloroform in a pyrex flask, and irradiating with a 300 nm Rayonet lamp for periods between 30 min and 1 h. Samples irradiated less than 30 min showed incomplete conversion. Referring to FIG. 18, attempts to perform isomerizations in different solvents 1802, 1804, in the absence of any solvent 1806, and simple exposure to ambient light 1808, resulted in IR reflectance spectra consistent with little or no signs of isomerization.

Examples 2-5

In Examples 2-5 suitable organic tethering molecules, surface coupling groups, head groups, tail portions, metals, and photochromic molecules include any of those described herein.

Example 2

Formation of Molecular Films on Non-Oxidized Metal Surface

Figure 20:
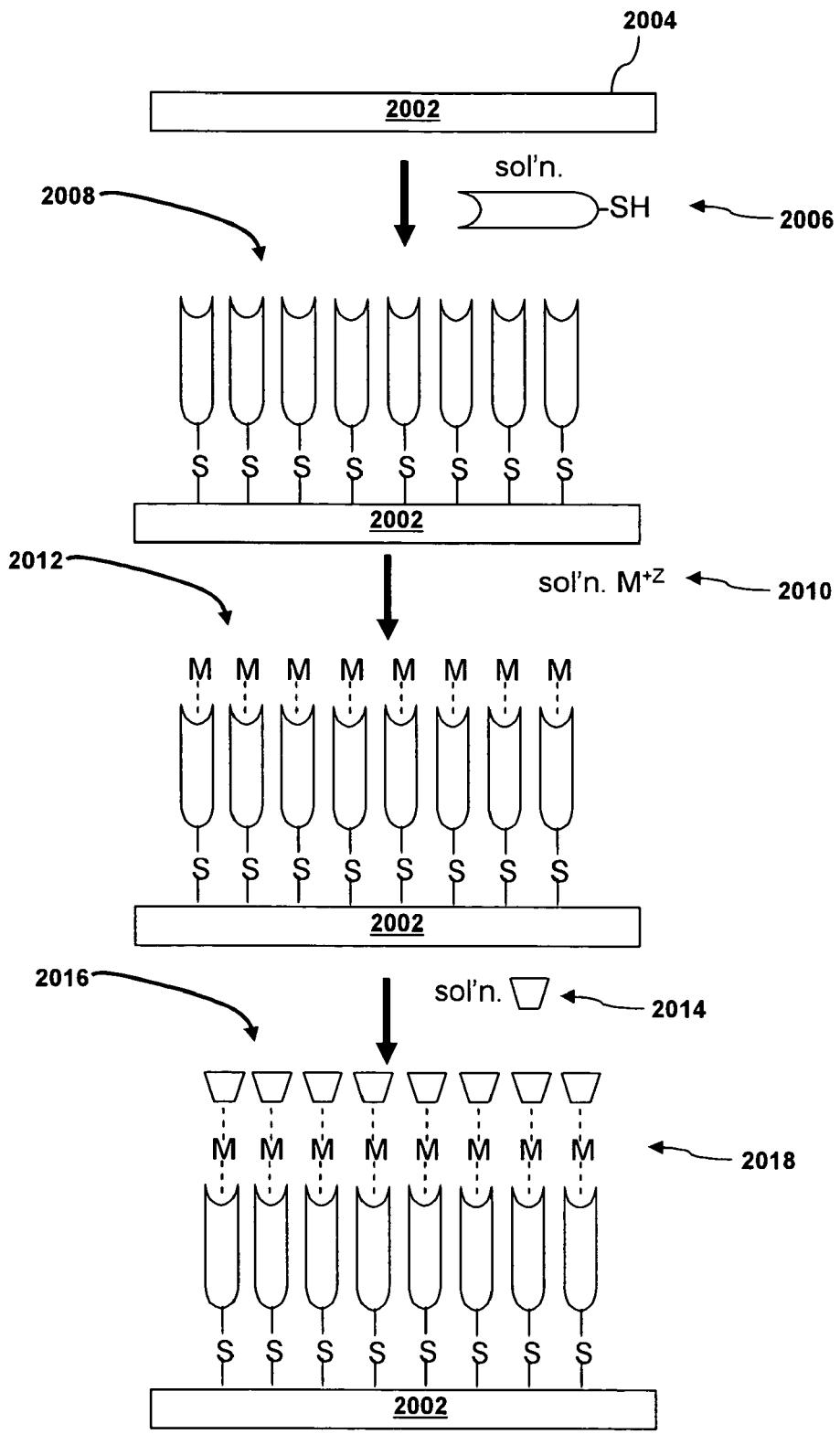
FIG. 20 depicts a schematic flow diagram of various embodiments of methods for forming a substantially monolayer thick photochromic film of the present invention on a non-oxidized metal surface.

Referring to FIG. 20, in various embodiments, a method for forming a substantially monolayer thick molecular film of the present invention on a substrate 2002 having a non-oxidized metal surface 2004 (e.g., gold, silver, platinum, etc.), comprises the steps of contacting the surface 2004 with a solution containing an organic tethering molecule, (e.g., of general formula (III)), or coupling group, 2006 having a thiol surface coupling group (here —SH), to produce a substantially monolayer thick organic tethering molecule, or coupling group, surface 2008. Preferably, the surface 2008 is rinsed with a suitable solvent to remove, e.g., impurities and unattached organic tethering molecules or coupling groups, and substantially dried prior to the next step.

After the surface 2004 is coated with the organic tethering molecule, or coupling group, surface 2008 to the extent desired, the surface 2008 is contacted with a solution containing metals ion M 2010, having charge state +Z, where Z is 1-6, (but preferably 2 for transition metal ions and preferably 4 for lead), to coordinate the metal atoms to the surface 2008 to produce a M coordinated organic tethering molecule, or coupling group, surface 2012. Preferably, the surface 2012 is rinsed with a suitable solvent to remove, e.g., impurities and unattached metal atoms, and substantially dried prior to the next step.

After the surface 2008 is coated with the metal atoms to the extent desired, the M coordinated organic tethering molecule, or coupling group, surface 2012 is contacted with a solution containing one or more photochromic molecules 2014, to coordinate the photochromic molecules to the surface 2012 to produce a substantially monolayer thick molecular film 2016 comprising one or more molecules of formulae (I), (II), (VI), (VII), (VIII), and combinations thereof 2018.

Example 3

Formation of Molecular Films on a Silicon Surface

Figure 21:
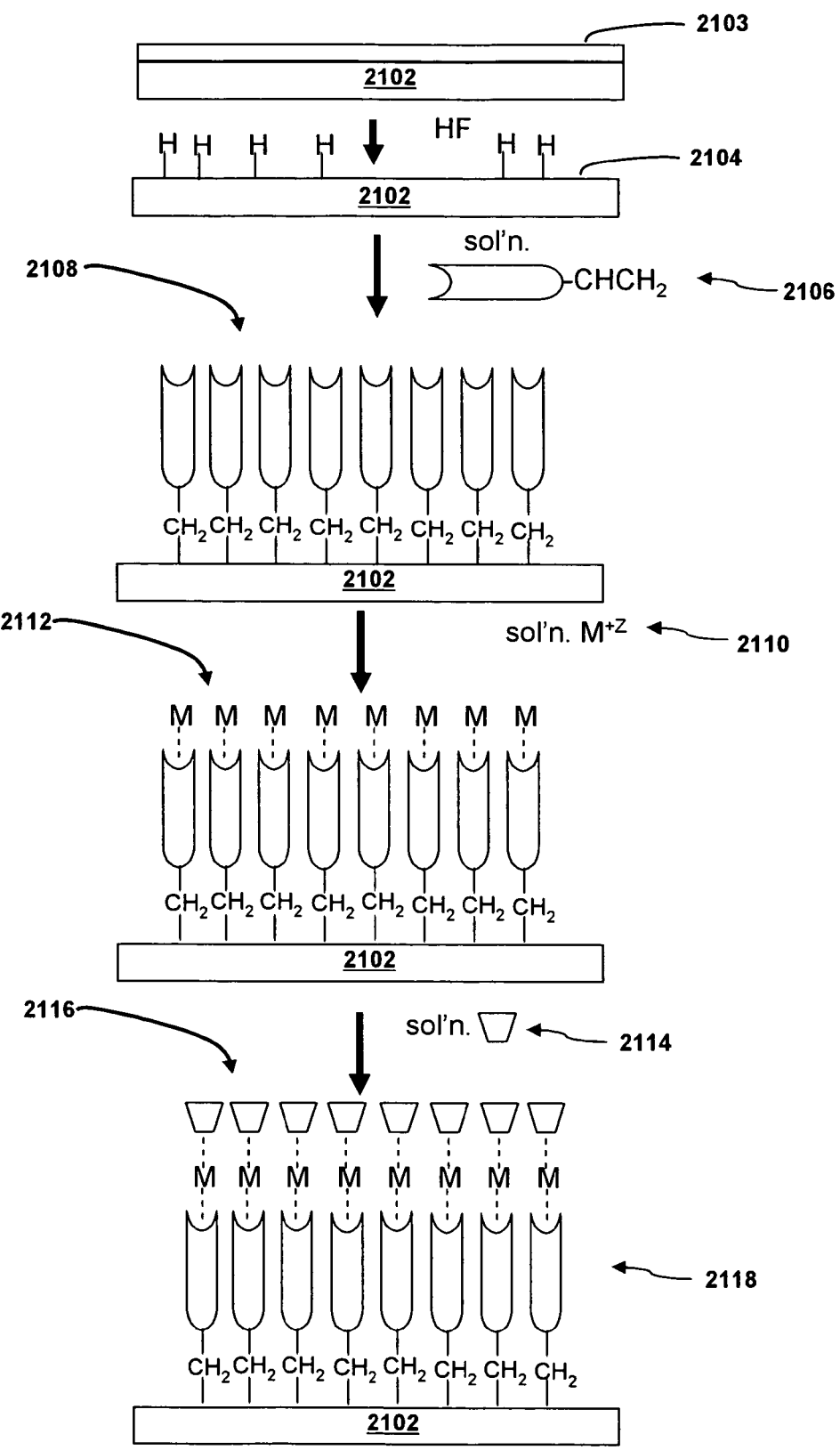
FIG. 21 depicts a schematic flow diagram of various embodiments of methods for forming a substantially monolayer thick photochromic film of the present invention on a silicon surface.

Referring to FIG. 21, in various embodiments, a method for forming a substantially monolayer thick molecular film of the present invention on a silicon substrate 2102 having a oxidized surface ($SiO_2$) 2103 is illustrated. In various embodiments, the oxidized surface 2103 is removed by reaction with acid (e.g., HF) to produce a substantially hydrogen terminated surface 2104 The method next comprises the steps of contacting the surface 2104 with a a solution containing an organic tethering molecule, (e.g., of general formula (III)), or coupling group, 2106 having an alkenyl surface coupling group (here —$CHCH_2$), to produce a substantially monolayer thick organic tethering molecule, or coupling group, surface 2108. Preferably, the surface 2108 is rinsed with a suitable solvent to remove, e.g., impurities and unattached organic tethering molecules or coupling groups, and substantially dried prior to the next step.

After the surface 2104 is coated with the organic tethering molecule, or coupling group, surface 2108 to the extent desired, the surface 2108 is contacted with a solution containing metals ion M 2110, having charge state +Z, where Z is 1-6, (but preferably 2 for transition metal ions and preferably 4 for lead), to coordinate the metal atoms to the surface 2108 to produce a M coordinated organic tethering molecule, or coupling group, surface 2112. Preferably, the surface 2112 is rinsed with a suitable solvent to remove, e.g., impurities and unattached metal atoms, and substantially dried prior to the next step.

After the surface 2108 is coated with the metal atoms to the extent desired, the M coordinated organic tethering molecule, or coupling group, surface 2112 is contacted with a solution containing one or more photochromic molecules 2114, to coordinate the photochromic molecules to the surface 2112 to produce a substantially monolayer thick molecular film 2116 comprising one or more molecules of formulae (I), (II), (VI), (VII), (VIII), and combinations thereof 2118.

Example 4

Figure 22:
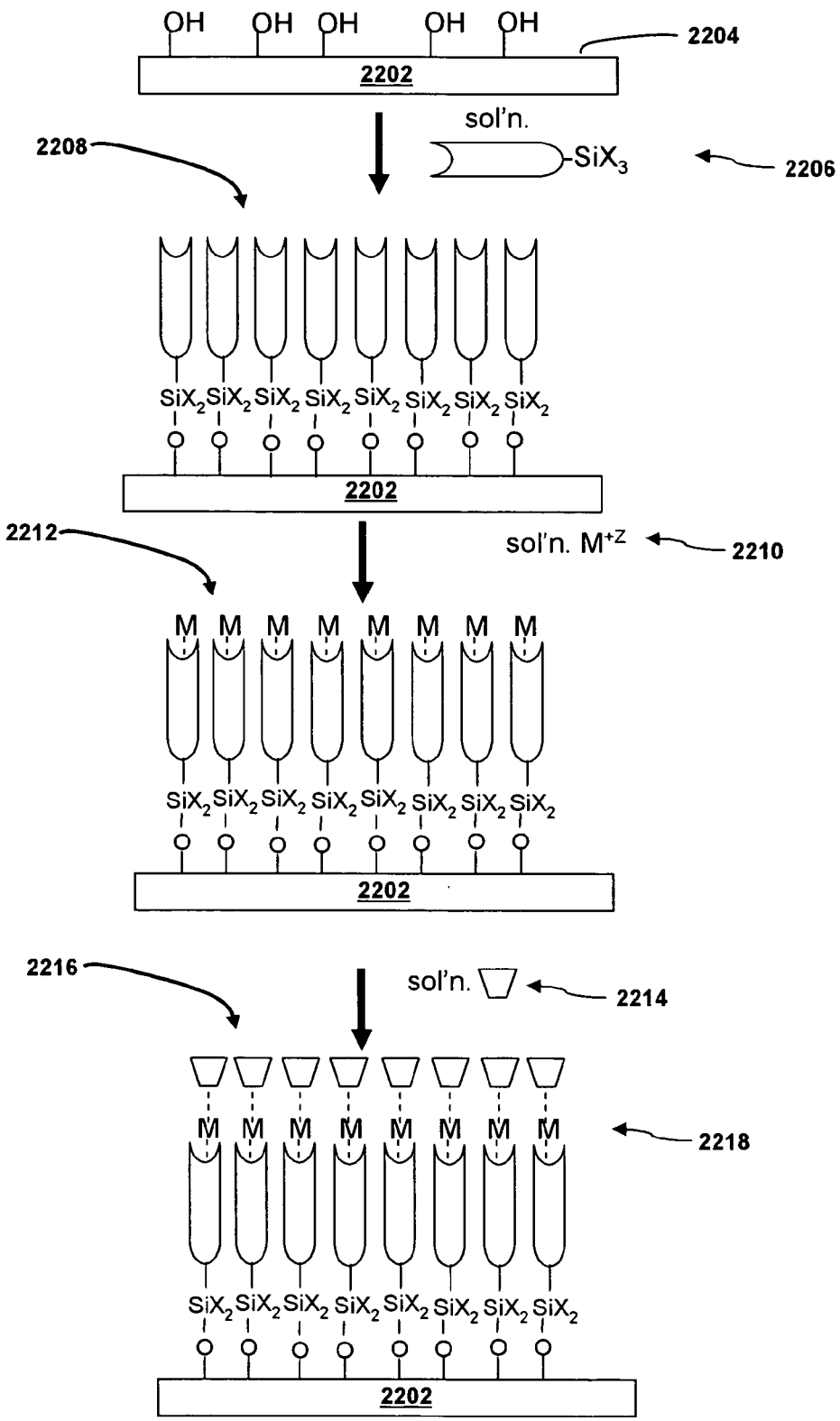
FIG. 22 depicts a schematic flow diagram of various embodiments of methods for forming a substantially monolayer thick photochromic film of the present invention on a glass, ORMOSIL gel, and/or metal oxide surface.

Formation of Molecular Films on a Glass, ORMOSIL Gel, and/or Metal Oxide Surface Referring to FIG. 22, in various embodiments, a method for forming a substantially monolayer thick molecular film of the present invention on a substrate 2002 having a glass, ORMOSIL gel, and/or metal oxide surface 2204, comprises the steps of contacting the surface 2204 with a solution containing an organic tethering molecule, (e.g., of general formula (III)), or coupling group, 2206 having a $SiX_3$ or where, in this example, X is independently, Cl, Br, I, or OR and where R=alkyl, to produce a substantially monolayer thick organic tethering molecule, or coupling group, surface 2208. Preferably, the surface 2208 is rinsed with a suitable solvent to remove, e.g., impurities and unattached organic tethering molecules or coupling groups, and substantially dried prior to the next step.

After the surface 2204 is coated with the organic tethering molecule, or coupling group, surface 2208 to the extent desired, the surface 2208 is contacted with a solution containing metals ion M 2210, having charge state +Z, where Z is 1-6, (but preferably 2 for transition metal ions and preferably 4 for lead), to coordinate the metal atoms to the surface 2208 to produce a M coordinated organic tethering molecule, or coupling group, surface 2212. Preferably, the surface 2212 is rinsed with a suitable solvent to remove, e.g., impurities and unattached metal atoms, and substantially dried prior to the next step.

After the surface 2008 is coated with the metal atoms to the extent desired, the M coordinated organic tethering molecule, or coupling group, surface 2212 is contacted with a solution containing one or more photochromic molecules 2214, to coordinate the photochromic molecules to the surface 2212 to produce a substantially monolayer thick molecular film 2216 comprising one or more molecules of formulae (I), (II), (VI), (VII), (VIII), and combinations thereof 2218.

Example 5

Formation of Molecular Films on a Polymer, Plastic or OH Functionalized Surface

Figure 23:
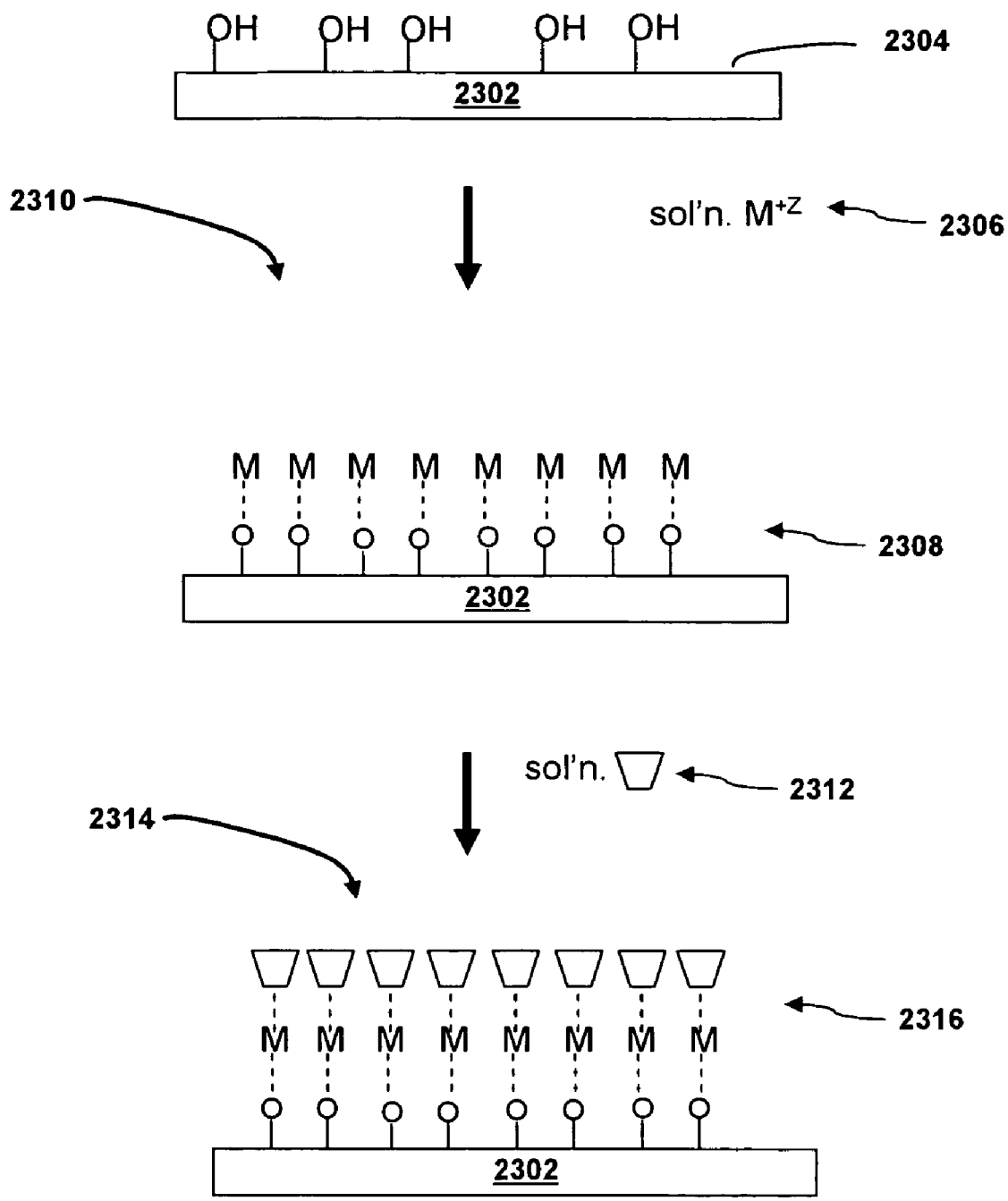
FIG. 23 depicts a schematic flow diagram of various embodiments of methods for forming a substantially monolayer thick photochromic film of the present invention on a polymer, plastic or OH functionalized surface.

Referring to FIG. 23, in various embodiments, a method for forming a substantially monolayer thick molecular film of the present invention on a substrate 2302 having a polymer, plastic or OH functionalized surface 2304 comprises the steps of contacting the surface 2304 with a solution containing metals ion M 2306, having charge state +Z, where Z is 1-6, (but preferably 2 for transition metal ions and preferably 4 for lead), to coordinate the metal atoms to oxygen atoms on the surface 2308 to produce a M coordinated surface 2310. Preferably, the surface 2310 is rinsed with a suitable solvent to remove, e.g., impurities and unattached metal atoms, and substantially dried prior to the next step.

After the surface 2310 is coated with the metal atoms to the extent desired, the M coordinated surface 2310 is contacted with a solution containing one or more photochromic molecules 2312, to coordinate the photochromic molecules to the surface 2312 to produce a substantially monolayer thick molecular film 2314 comprising one or more molecules of, e.g., formulae (II) 2316.

All literature and similar material cited in this application, including, patents, patent applications, articles, books, treatises, and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. By way of example, any of the disclosed features can be combined with any of the other disclosed features to provide a substantially monolayer thick molecular film in accordance with the present inventions. For example, any of the various disclosed embodiments of a photochromic molecule can be combined with any one or more metal atom, and any one or more of an organic tethering molecule, coupling group, or both, to provide a substantially monolayer thick molecular film with photoresponsive wettability in accordance with one or more embodiments of the present inventions. Therefore, all embodiments that come within the scope and spirit of the following claims and equivalents thereto are claimed.

What is claimed is:

1. A substantially monolayer thick molecular film comprising self assembled molecules of the general formula (I): $R_1$—M—$R_2(X)_m R_3 R_4$, wherein,
   $R_1$ represents a photochromic molecule coordinated to M;
   M represents a transition metal atom substantially of oxidation state Y a lanthanide metal atom substantially of oxidation state Z or a lead (Pb) atom of oxidation state IV;
   Y represents oxidation state I, II, III, IV, V, or VI;
   Z represents oxidation state I, II, III, IV, V, or VI;
   $R_2$ represents an unsubstituted heterocyclic group coordinated to M, a substituted heterocyclic group coordinated to M, or a substituted aryl group coordinated to M (wherein the substituted aryl group is substituted with one or of more oxygen, nitrogen or oxygen and nitrogen containing substituents from the substituent group A);
   the dashed line represents the coordination of one or more donor atoms to M;
   X represents a —NH—, —O—, or —S—;
   m represents 0 or 1;
   $R_3$ represents an alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof;
   $R_4$ represents a bond, —O—, —S—, —P—, —CH$_2$—, —OSi(OR$_5$)$_2$ or —OSiCl$_2$—;
   $R_5$ represents an alkyl; and
   substituent group A comprises an alkoxyl group, an amide group, an amino group, a carbonyl group, a carboxyl group, a hydroxyl group, and a heterocyclic group.

2. The substantially monolayer thick molecular film of claim 1, wherein the photochromic molecule comprises an unsubstituted or substituted spiropyran molecule.

3. The substantially monolayer thick molecular film of claim 2, wherein the spiropyran molecule comprises a closed form, an open form, or both of an unsubstituted or substituted 6-nitro-1',3',3'-trimethylspiro (2H- 1-benzopyran-2,2'indoline).

4. The substantially monolayer thick molecular film of claim 1, wherein the photochromic molecule comprises an unsubstituted or substituted spirooxazine molecule.

5. The substantially monolayer thick molecular film of claim 1, wherein the photochromic molecule comprises a dipyridyl containing molecule.

6. The substantially monolayer thick molecular film of claim 5, wherein the photochromic molecule comprises an unsubstituted or substituted 2,2'-dipyridylethylene.

7. The substantially monolayer thick molecular film of claim 1, wherein the photochromic molecule comprises an unsubstituted or substituted chromene molecule.

8. The substantially monolayer thick molecular film of claim 1, wherein the photochromic molecule comprises an unsubstituted or substituted spirodihydroindolizine molecule.

9. The substantially monolayer thick molecular film of claim 1, wherein the photochromic molecule comprises a substituted diazene molecule.

10. The substantially monolayer thick molecular film of claim 1, wherein M comprises Cu(II), Co(II), Mn(II), Ni(II) or Zn(II).

11. The substantially monolayer thick molecular film of claim 1, wherein $R_2$ comprises a dicarboxypyridine.

12. The substantially monolayer thick molecular film of claim 1, wherein $R_3$ comprise a $C_{10}$-$C_{16}$ alkyl group.

13. The substantially monolayer thick molecular film of claim 1, wherein $R_2$-$(X)_m$-$R_3$ together comprise 4-(decyloxy)pyridine-2,6-dicarboxylic acid.

14. The substantially monolayer thick molecular film of claim 1, wherein the photochromic molecule has substantially reversible photoresponsive wettability.

15. The substantially monolayer thick molecular film of claim 1, wherein the photochromic molecule has a substantially irreversible photoresponsive wettability.

16. The substantially monolayer thick molecular film of claim 1, wherein the photochromic molecule has a change in surface wettability of greater than about 10° between two or more configurations of the photochromic molecule.

17. The substantially monolayer thick molecular film of claim 1, wherein the photochromic molecule has a change in surface wettability of greater than about 15° between two or more configurations of the photochromic molecule.

18. The substantially monolayer thick molecular film of claim 1, wherein $R_4$ is —S— when the surface of a substrate on which the substantially monolayer thick molecular film is attached comprises gold; wherein $R_4$ is —P— when the surface of a substrate on which the substantially monolayer thick molecular film is attached comprises GaAs or GaN; is —CH$_2$— when the surface of a substrate on which the substantially monolayer thick molecular film is attached comprises silicon, and is —OSiCl$_2$— when the surface of a substrate on which the substantially monolayer thick molecular film is attached comprises silicon dioxide.

19. A photochromic article having a surface portion with a photoresponsive wettability, the photochromic article comprising:
   a substrate having a surface;
   a substantially monolayer thick molecular film covering at least a portion of the surface; the substantially monolayer thick molecular film having a photoresponsive wettability and comprising molecules of the general formula (I): R$_1$—M—R$_2$(X)$_m$R$_3$R$_4$, the molecules being attached to a surface of the substrate via R$_4$, wherein,
   R$_1$ represents a photochromic molecule coordinated to M;
   M represents a transition metal atom substantially of oxidation state Y a lanthanide metal atom substantially of oxidation state Z or a lead (Pb) atom of oxidation state IV;
   Y represents oxidation state I, II, III, IV, V, or VI;
   Z represents oxidation state I, II, III, IV, V, or VI;
   R$_2$ represents an unsubstituted heterocyclic group coordinated to M, a substituted heterocyclic group coordinated to M, or a substituted aryl group coordinated to M (wherein the substituted aryl group is substituted with one or of more oxygen, nitrogen or oxygen and nitrogen containing substituents from the substituent group A); the dashed line represents the coordination of one or more donor atoms to M;
   X represents a —NH—, —O—, or —S—; m represents 0 or 1;
   R$_3$ represents an alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphonato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof;
   R$_4$ represents a bond, —O—, —S—, —P—, —CH$_2$—, —OSi(OR$_5$)$_2$ or —OSiCl$_2$—;
   R$_5$ represents an alkyl; and
   substituent group A comprises an alkoxyl group, an amide group, an amino group, a carbonyl group, a carboxyl group, a hydroxyl group, and a heterocyclic group.

20. A method of making the article of claim 19 by forming on a surface a substantially monolayer thick molecular film having a photoresponsive wettability, the method comprising the steps of:

contacting the surface of a substrate with a solution containing a organic tethering molecule, the organic tethering molecule having the general formula (III) below, $$R_2(X)_m R_3 R_4 \quad (III),$$

rinsing with a solvent and substantially drying the organic tethering molecule surface;
   contacting the organic tethering molecule surface with a solution containing a metal ion M, wherein M comprises a transition metal ion of oxidation state I, II, III, IV, V, or VI, a lanthanide metal ion of oxidation state I, II, III, IV, V, or VI, or a lead ion of oxidation state IV;
   rinsing with a solvent and substantially drying the M coordinated organic tethering molecule surface; and
   contacting the M coordinated organic tethering molecule surface with a solution containing a photochromic molecule;
   wherein,
   R$_2$ represents an unsubstituted heterocyclic group coordinated to M, a substituted heterocyclic group coordinated to M, or a substituted aryl group coordinated to M (wherein the substituted aryl group is substituted with one or more oxygen, nitrogen or oxygen and nitrogen containing substituents from the substituent group A); the dashed line represents the coordination of one or more donor atoms to M;
   X represents a —NH—, —O—, or —S—;
   m represents 0 or 1;
   R$_3$ represents an alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphonato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof;
   R$_4$ represents a bond, —O—, —S—, —P—, —CH$_2$—, —OSi(OR$_5$)2 or —OSiCl$_2$—;
   R$_5$ represents an alkyl; and
   substituent group A comprises an alkoxyl group, an amide group, an amino group, a carbonyl group, a carboxyl group, a hydroxyl group, and a heterocyclic group.

* * * * *